(12) United States Patent
Ajona Martínez-Polo et al.

(10) Patent No.: US 10,545,150 B2
(45) Date of Patent: Jan. 28, 2020

(54) LUNG CANCER MOLECULAR MARKERS

(71) Applicant: PROYECTO DE BIOMEDICINA CIMA, S.L., Pamplona (ES)

(72) Inventors: Daniel Ajona Martínez-Polo, Pamplona (ES); Leticia Corrales Pecino, Pamplona (ES); Luis Montuenga Badía, Pamplona (ES); María José Pajares Villandiego, Pamplona (ES); Rubén Pío Osés, Pamplona (ES)

(73) Assignee: PROYECTO DE BIOMEDICINA CIMA, S.L., Pamplona (ES)

( * ) Notice: Subject to any disclaimer, the term of this patent is extended or adjusted under 35 U.S.C. 154(b) by 39 days.

(21) Appl. No.: 14/388,791

(22) PCT Filed: Mar. 20, 2013

(86) PCT No.: PCT/EP2013/055823
§ 371 (c)(1),
(2) Date: Sep. 26, 2014

(87) PCT Pub. No.: WO2013/143940
PCT Pub. Date: Oct. 3, 2013

(65) Prior Publication Data
US 2015/0072361 A1 Mar. 12, 2015

(30) Foreign Application Priority Data
Mar. 29, 2012 (EP) ..................... 12382113

(51) Int. Cl.
*G01N 33/574* (2006.01)
(52) U.S. Cl.
CPC .......... *G01N 33/57423* (2013.01); *G01N 2333/4716* (2013.01); *G01N 2800/52* (2013.01)
(58) Field of Classification Search
CPC ..... G01N 33/57423; G01N 2333/4716; G01N 2800/52
See application file for complete search history.

(56) References Cited

U.S. PATENT DOCUMENTS

| | | | |
|---|---|---|---|
| 2005/0042602 A1* | 2/2005 | Ahearn ................... | G01N 33/80 435/5 |
| 2010/0070191 A1* | 3/2010 | Gold ................ | G01N 33/57423 702/19 |
| 2010/0233704 A1* | 9/2010 | Michot ................ | C12Q 1/6886 435/6.11 |

FOREIGN PATENT DOCUMENTS

| | | |
|---|---|---|
| KR | 100899848 B1 | 5/2009 |
| KR | 100925147 B1 | 11/2009 |

OTHER PUBLICATIONS

Vachino et al., Complement Activation in Cancer Patients Undergoing Immunotherapy With Interleukin-2 (IL-2): Binding of Complement and C-Reactive Protein by IL- 2-Activated Lymphocytes, Blood, vol. 78, No. 10 (Nov. 15, 1991: pp. 2505-2513.*
Oner et al., Immunoglobulins and Complement Components in Patients with Lung Cancer, Tüberküloz ve Toraks Dergisi 2004; 52(1): 19-23.*
Gminski et al., Immunoglobulins and Complement Components Levels in Patients with Lung Cancer, Rev. Roum. Med. Int. 1992, 30, 39-44.*
Wen et al., Development of an AlphaLISA assay to quantify serum core-fucosylated E-cadherin as a metastatic lung adenocarcinoma biomarker, Journal of Proteomics 75 (2012) 3963-3976.*
Pietrowska et al., Comparison of peptide cancer signatures identified by mass spectrometry in serum of patients with head and neck, lung and colorectal cancers: Association with tumor progression, International Journal of Oncology 40: 148-156, 2012.*
Vallhonrat et al., In Vivo Generation of C4d,Bb, iC3b, and SC5b-9 After OKT3 Administration in Kidney and Lung Transplant Recipients, Transplantation: Jan. 27, 1999—vol. 67—Issue 2—p. 253-258, p. 1-8. (Year: 1999).*
Cicenas et al., Lung cancer in patients with tuberculosis, World Journal of Surgical Oncology 2007, 5:22, 1-5. (Year: 2007).*
Ajona, Daniel "Activation of the classical complement pathway in lung cancer: A novel biomarker for diagnosis and prognosis," Abstracts/Immunobiology, vol. 217, No. 11, 2012, p. 1135, XP055063986, ISSN: 0171-2985, DOI: 10.1016fj.imbio.2012.08. 019.
Gminski J et al: "Immunoglobulins and Complement Components Levels in Patients with Lung Cancer," Rev. Roum. Med. Int., 1992, vol. 30, No. 1, pp. 39-44, XP008162417, ISSN: 1220-4749 tables I,VI.

(Continued)

*Primary Examiner* — Andrea S Grossman
(74) *Attorney, Agent, or Firm* — Squire Patton Boggs (US) LLP

(57) ABSTRACT

The invention provides a method of diagnosis and/or prognosis of lung cancer, the method comprising the steps of: (a) determining the level of a C4 activation fragment in a test sample, and (b) comparing the level of the test sample with the level of a C4 activation fragment detected in a control sample, wherein if the level of C4 activation fragment is higher than the level in a reference control, it is indicative that the subject suffers lung cancer or has a bad prognosis. The present invention further provides methods for determining the risk of suffering from lung cancer as well as for deciding whether to initiate a medical regimen and to determine the efficacy of said medical regimen, based on the determination of a C4 activation fragment.
C4 activation fragment, used as marker, confers high sensitivity and specificity to the methods object of the invention.

14 Claims, 18 Drawing Sheets
Specification includes a Sequence Listing.

(56) References Cited

OTHER PUBLICATIONS

International Search Report and Written Opinion in PCT/EP2013/055823, dated Jun. 6, 2013, 13 pages.
Oner F. et al., "Immunoglobulins and Complement Components in Patients with Lung Cancer", Tuberk Toraks, 2004, vol. 52, pp. 19-23.
Aberle et al., "Reduced Lung-Cancer Mortality with Low-Dose Computed Tomographic Screening," *N. Engl. J. Med.*, Aug. 4, 2011, vol. 365, pp. 395-409.
Ajona D. et al., "Complement activation product C4d in Oral and Oropharyngeal Squamous Cell Carcinoma", *Oral Diseases*, 2015, vol. 21, pp. 899-904.
Ajona D., "Activation of the classical complement pathway in lung cancer: A novel biomarker for diagnosis and prognosis," Abstracts/Immunobiology, vol. 217, No. 11, 2012, p. 1135, XP055063986, ISSN: 0171-2985, DOI: 10.1016fj.imbio.2012.08.019.
Burtis et al., "Chapter 14: Establishment and Use of Reference Values," Tietz Fundamentals of Clinical Chemistry, 6$^{th}$ ed., Saunders/Elsevier, 2008, pp. 229-238.
Henschke et al., "Early Lung Cancer Action Project: overall design and findings from baseline screening", *The Lancet*, Jul. 10, 1999, vol. 354, pp. 99-105.
Henschke et al., "Survival of Patients with Stage I Lung Cancer Detected on CT Screening," *N. Engl. J. Med.*, Oct. 26, 2006, vol. 355, No. 17, pp. 1763-1771.
Hou et al., "Preparation of $C_4$ Antiserum and Detection of Complement $C_4$ Activation in Plasma with Crossed Immunoelectrophoresis," Dec. 1985, vol. 7, No. 6, pp. 473-474.
Matsutani et al., "Cellular Immunity and Complement Levels in Hosts with Brain Tumours", *Neurosurg. Rev.* 7, 1984, pp. 29-35.
Niehans et al., "Human Carcinomas Variably Express the Complement Inhibitory Proteins CD46 (Membrane Cofactor Protein), CD55 (Decay-Accelerating Factor), and CD59 (protectin)," *Am. J. Pathol.*, 1996, vol. 149, No. 1, pp. 129-142.
Nishioka K et al.,"The Complement System in Tumor Immunity: Significance of Elevated Levels of Complement in Tumor Bearing Hosts," *Annals New York Academy of Sciences*, 1976, vol. 276, pp. 303-315.
Pio R. "Control of Complement Activation by Cancer Cells and its Implications in Antibody-Mediated Cancer Immunotherapy," *Immunologia*, Sep. 5, 2006, vol. 25, No. 3, pp. 173-187.
Pio R. et al., "Complement Factor H is Elevated in Bronchoalveolar Lavage Fluid and Sputum from Patients with Lung Cancer," *Cancer Epidemiol Viomarkers Prev.*, 2010, vol. 19, No. 10, pp. 2665-2672.
Saito et al., "Increases in Immunoglobulin and Complement in Patients with Esophageal or Gastric Cancer", *Surgery Today*, Jpn. J. Surg., 1992, vol. 22, pp. 537-542.
Travis et al., World Health Organization Classification of Tumours. Pathology and Genetics of Tumours of the Lung, Pleura, Thymus and Heart. Lyon: IARC Press; 2004.
Unknown: "Complement component 4" Wikipedia, the free encyclopedia, Aug. 4, 2011, 3 pages, XP055064790, Retrieved from the Internet: URL:http://en.wikipedia.org/wiki/Complement component 4 [retrieved on May 31, 2013] the whole document.

* cited by examiner

FIG. 4 (Continuation)
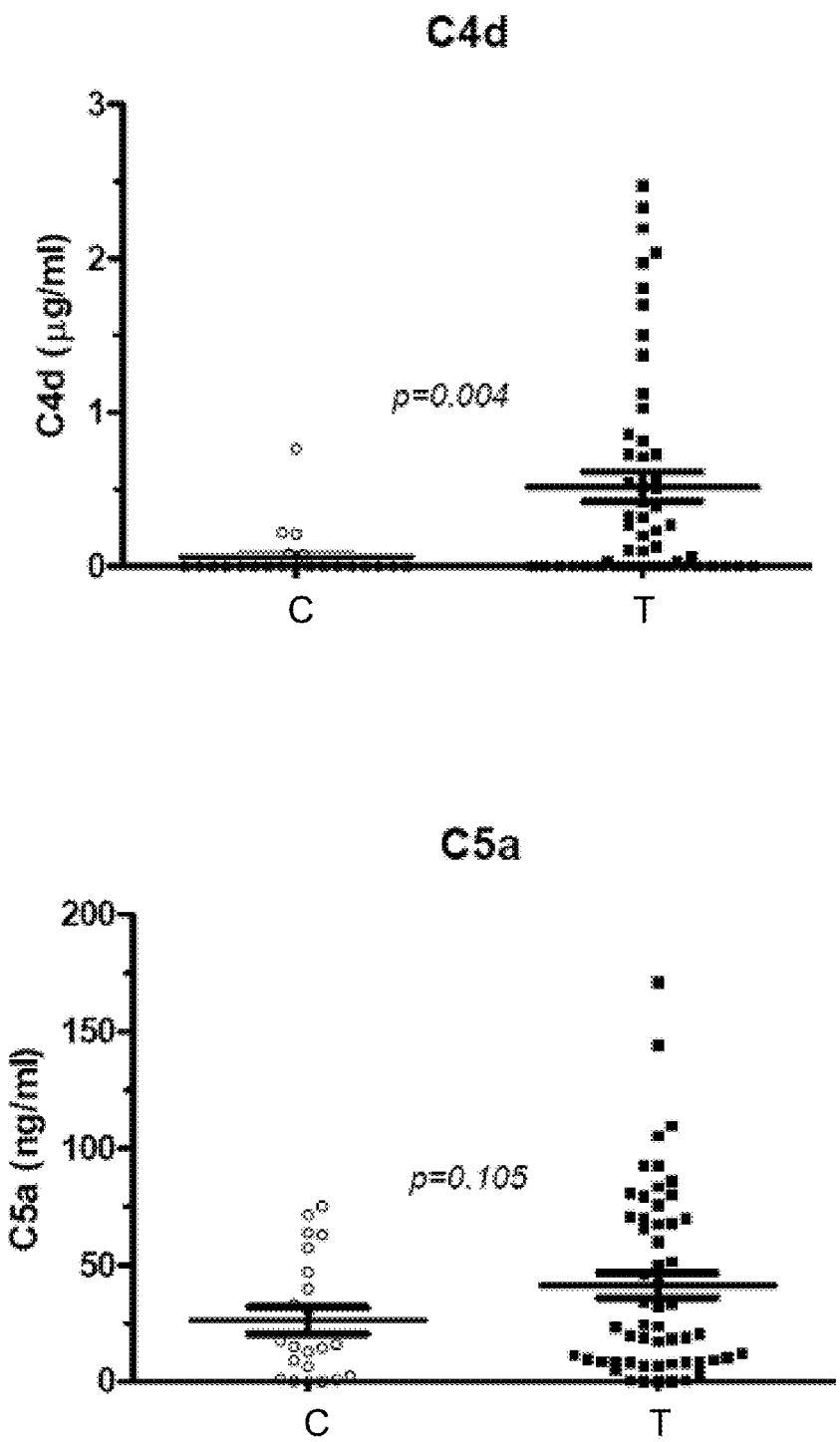

FIG. 5 (Continuation)
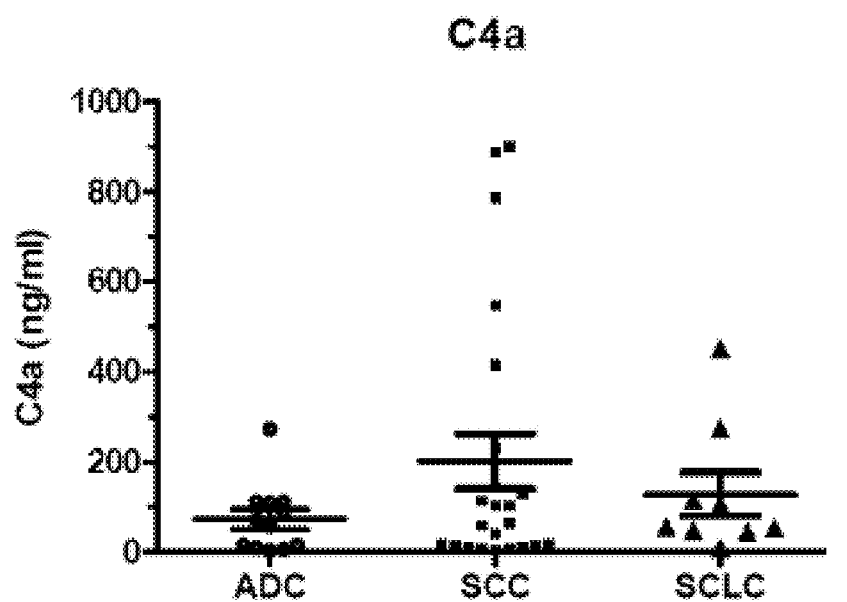
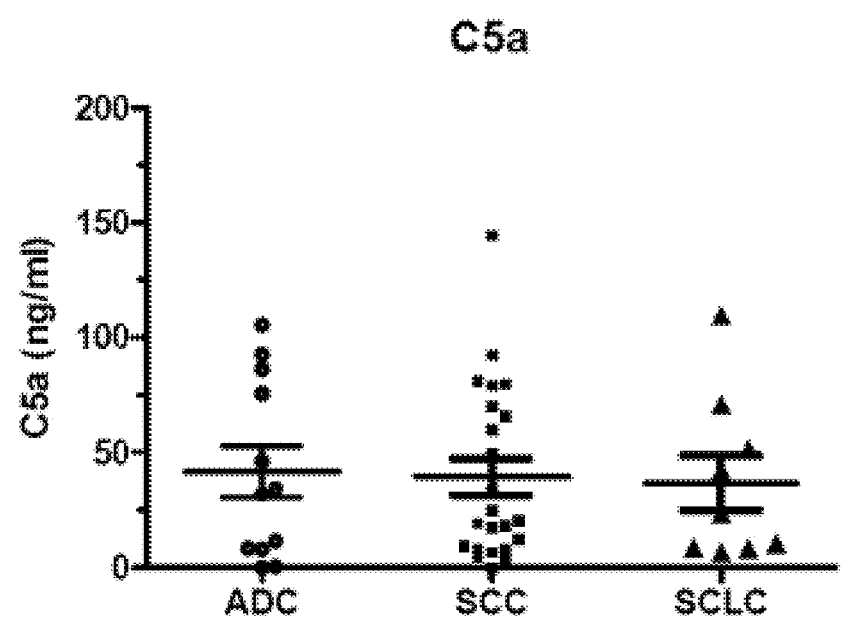

FIG. 6 (Continuation)
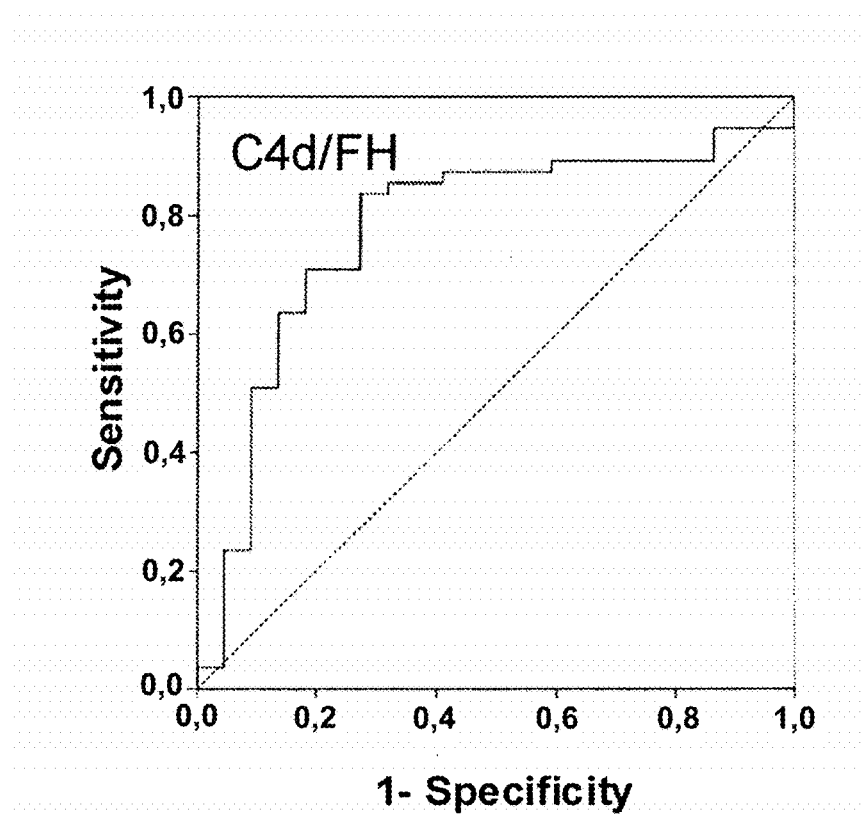
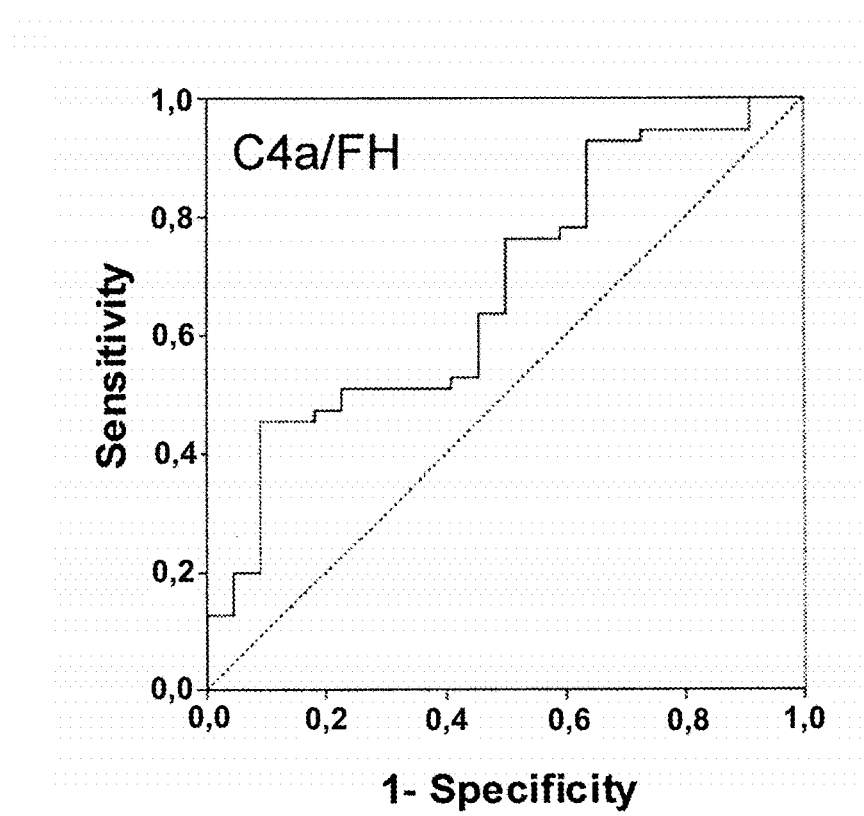

FIG. 7 (Continuation)
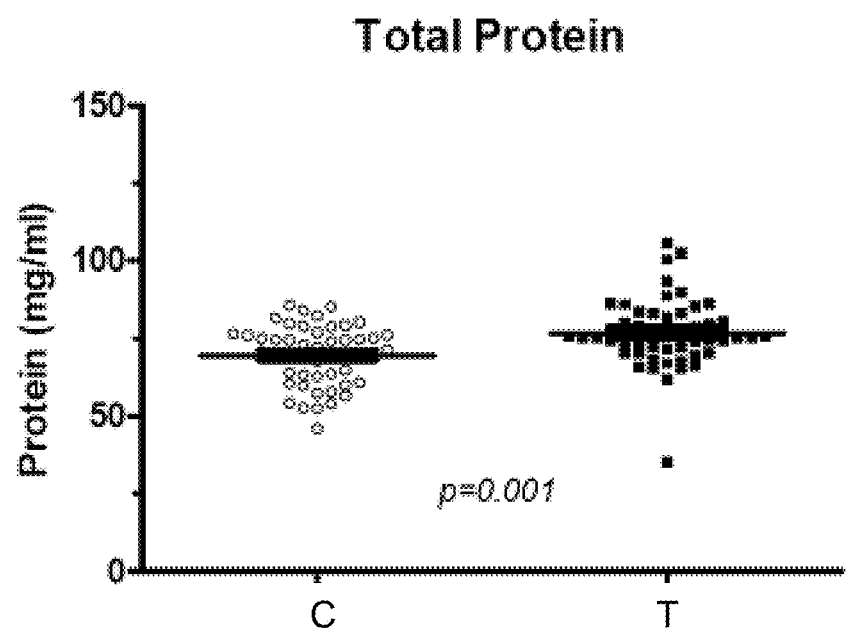

FIG. 9 (Continuation)
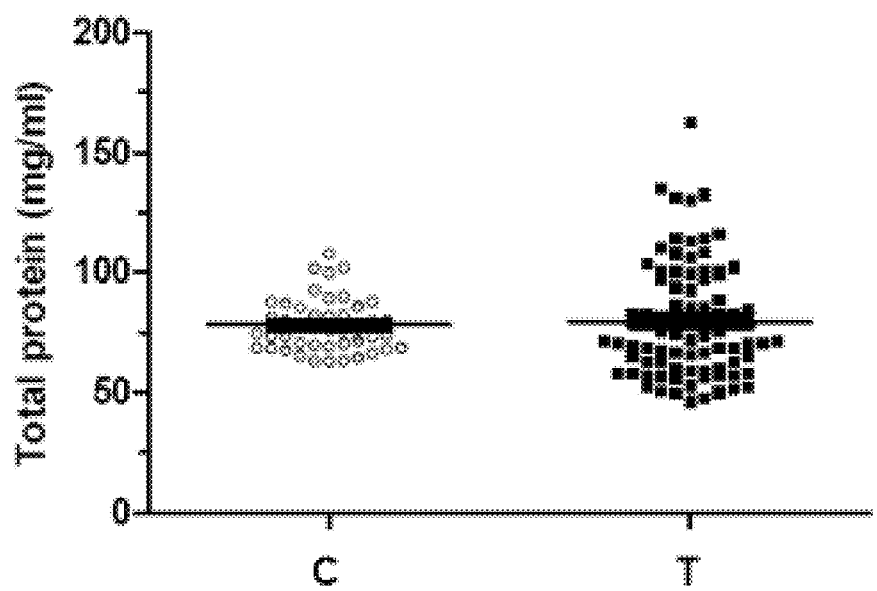

SEQUENCE LISTING

```
<160> NUMBER OF SEQ ID NOS: 5

<210> SEQ ID NO 1
<211> LENGTH: 380
<212> TYPE: PRT
<213> ORGANISM: Homo sapiens
<300> PUBLICATION INFORMATION:
<308> DATABASE ACCESSION NUMBER: Uniprot / P0C0L4
<309> DATABASE ENTRY DATE: 1986-07-21
<313> RELEVANT RESIDUES IN SEQ ID NO: (957)..(1336)

<400> SEQUENCE: 1

Thr Leu Glu Ile Pro Gly Asn Ser Asp Pro Asn Met Ile Pro Asp Gly
1               5                   10                  15

Asp Phe Asn Ser Tyr Val Arg Val Thr Ala Ser Asp Pro Leu Asp Thr
            20                  25                  30

Leu Gly Ser Glu Gly Ala Leu Ser Pro Gly Gly Val Ala Ser Leu Leu
        35                  40                  45

Arg Leu Pro Arg Gly Cys Gly Glu Gln Thr Met Ile Tyr Leu Ala Pro
    50                  55                  60

Thr Leu Ala Ala Ser Arg Tyr Leu Asp Lys Thr Glu Gln Trp Ser Thr
65                  70                  75                  80

Leu Pro Pro Glu Thr Lys Asp His Ala Val Asp Leu Ile Gln Lys Gly
                85                  90                  95

Tyr Met Arg Ile Gln Gln Phe Arg Lys Ala Asp Gly Ser Tyr Ala Ala
            100                 105                 110

Trp Leu Ser Arg Asp Ser Ser Thr Trp Leu Thr Ala Phe Val Leu Lys
        115                 120                 125

Val Leu Ser Leu Ala Gln Glu Gln Val Gly Gly Ser Pro Glu Lys Leu
    130                 135                 140

Gln Glu Thr Ser Asn Trp Leu Leu Ser Gln Gln Gln Ala Asp Gly Ser
145                 150                 155                 160

Phe Gln Asp Pro Cys Pro Val Leu Asp Arg Ser Met Gln Gly Gly Leu
                165                 170                 175

Val Gly Asn Asp Glu Thr Val Ala Leu Thr Ala Phe Val Thr Ile Ala
            180                 185                 190

Leu His His Gly Leu Ala Val Phe Gln Asp Glu Gly Ala Glu Pro Leu
        195                 200                 205

Lys Gln Arg Val Glu Ala Ser Ile Ser Lys Ala Asn Ser Phe Leu Gly
    210                 215                 220

Glu Lys Ala Ser Ala Gly Leu Leu Gly Ala His Ala Ala Ala Ile Thr
225                 230                 235                 240

Ala Tyr Ala Leu Ser Leu Thr Lys Ala Pro Val Asp Leu Leu Gly Val
                245                 250                 255

Ala His Asn Asn Leu Met Ala Met Ala Gln Glu Thr Gly Asp Asn Leu
            260                 265                 270
```

```
Tyr Trp Gly Ser Val Thr Gly Ser Gln Ser Asn Ala Val Ser Pro Thr
            275                 280                 285

Pro Ala Pro Arg Asn Pro Ser Asp Pro Met Pro Gln Ala Pro Ala Leu
            290                 295                 300

Trp Ile Glu Thr Thr Ala Tyr Ala Leu Leu His Leu Leu His Glu
305                 310                 315                 320

Gly Lys Ala Glu Met Ala Asp Gln Ala Ser Ala Trp Leu Thr Arg Gln
                    325                 330                 335

Gly Ser Phe Gln Gly Gly Phe Arg Ser Thr Gln Asp Thr Val Ile Ala
                340                 345                 350

Leu Asp Ala Leu Ser Ala Tyr Trp Ile Ala Ser His Thr Thr Glu Glu
                    355                 360                 365

Arg Gly Leu Asn Val Thr Leu Ser Ser Thr Gly Arg
        370                 375                 380

<210> SEQ ID NO 2
<211> LENGTH: 380
<212> TYPE: PRT
<213> ORGANISM: Homo sapiens
<300> PUBLICATION INFORMATION:
<308> DATABASE ACCESSION NUMBER: Uniprot / P0C0L5
<309> DATABASE ENTRY DATE: 1986-07-21
<313> RELEVANT RESIDUES IN SEQ ID NO: (957)..(1336)

<400> SEQUENCE: 2

Thr Leu Glu Ile Pro Gly Asn Ser Asp Pro Asn Met Ile Pro Asp Gly
1               5                   10                  15

Asp Phe Asn Ser Tyr Val Arg Val Thr Ala Ser Asp Pro Leu Asp Thr
                20                  25                  30

Leu Gly Ser Glu Gly Ala Leu Ser Pro Gly Gly Val Ala Ser Leu Leu
            35                  40                  45

Arg Leu Pro Arg Gly Cys Gly Glu Gln Thr Met Ile Tyr Leu Ala Pro
        50                  55                  60

Thr Leu Ala Ala Ser Arg Tyr Leu Asp Lys Thr Glu Gln Trp Ser Thr
65                  70                  75                  80

Leu Pro Pro Glu Thr Lys Asp His Ala Val Asp Leu Ile Gln Lys Gly
                85                  90                  95

Tyr Met Arg Ile Gln Gln Phe Arg Lys Ala Asp Gly Ser Tyr Ala Ala
                    100                 105                 110

Trp Leu Ser Arg Asp Ser Ser Thr Trp Leu Thr Ala Phe Val Leu Lys
                115                 120                 125

Val Leu Ser Leu Ala Gln Glu Gln Val Gly Gly Ser Pro Glu Lys Leu
            130                 135                 140

Gln Glu Thr Ser Asn Trp Leu Leu Ser Gln Gln Gln Ala Asp Gly Ser
145                 150                 155                 160

Phe Gln Asp Leu Ser Pro Val Ile His Arg Ser Met Gln Gly Gly Leu
                165                 170                 175

Val Gly Asn Asp Glu Thr Val Ala Leu Thr Ala Phe Val Thr Ile Ala
                180                 185                 190

Leu His His Gly Leu Ala Val Phe Gln Asp Glu Gly Ala Glu Pro Leu
            195                 200                 205

Lys Gln Arg Val Glu Ala Ser Ile Ser Lys Ala Asn Ser Phe Leu Gly
        210                 215                 220

Glu Lys Ala Ser Ala Gly Leu Leu Gly Ala His Ala Ala Ala Ile Thr
225                 230                 235                 240

Ala Tyr Ala Leu Ser Leu Thr Lys Ala Pro Val Asp Leu Leu Gly Val
```

```
                    245                 250                 255
Ala His Asn Asn Leu Met Ala Met Ala Gln Glu Thr Gly Asp Asn Leu
            260                 265                 270

Tyr Trp Gly Ser Val Thr Gly Ser Gln Ser Asn Ala Val Ser Pro Thr
        275                 280                 285

Pro Ala Pro Arg Asn Pro Ser Asp Pro Met Pro Gln Ala Pro Ala Leu
        290                 295                 300

Trp Ile Glu Thr Thr Ala Tyr Ala Leu Leu His Leu Leu His Glu
305                 310                 315                 320

Gly Lys Ala Glu Met Ala Asp Gln Ala Ser Ala Trp Leu Thr Arg Gln
                325                 330                 335

Gly Ser Phe Gln Gly Gly Phe Arg Ser Thr Gln Asp Thr Val Ile Ala
            340                 345                 350

Leu Asp Ala Leu Ser Ala Tyr Trp Ile Ala Ser His Thr Thr Glu Glu
        355                 360                 365

Arg Gly Leu Asn Val Thr Leu Ser Ser Thr Gly Arg
        370                 375                 380

<210> SEQ ID NO 3
<211> LENGTH: 690
<212> TYPE: PRT
<213> ORGANISM: Homo sapiens

<400> SEQUENCE: 3

Ala Leu Glu Ile Leu Gln Glu Asp Leu Ile Asp Glu Asp Asp Ile
1               5                   10                  15

Pro Val Arg Ser Phe Phe Pro Glu Asn Trp Leu Trp Arg Val Glu Thr
            20                  25                  30

Val Asp Arg Phe Gln Ile Leu Thr Leu Trp Leu Pro Asp Ser Leu Thr
        35                  40                  45

Thr Trp Glu Ile His Gly Leu Ser Leu Ser Lys Thr Lys Gly Leu Cys
    50                  55                  60

Val Ala Thr Pro Val Gln Leu Arg Val Phe Arg Glu Phe His Leu His
65                  70                  75                  80

Leu Arg Leu Pro Met Ser Val Arg Arg Phe Glu Gln Leu Glu Leu Arg
                85                  90                  95

Pro Val Leu Tyr Asn Tyr Leu Asp Lys Asn Leu Thr Val Ser Val His
            100                 105                 110

Val Ser Pro Val Glu Gly Leu Cys Leu Ala Gly Gly Gly Gly Leu Ala
        115                 120                 125

Gln Gln Val Leu Val Pro Ala Gly Ser Ala Arg Pro Val Ala Phe Ser
    130                 135                 140

Val Val Pro Thr Ala Ala Ala Val Ser Leu Lys Val Val Ala Arg
145                 150                 155                 160

Gly Ser Phe Glu Phe Pro Val Gly Asp Ala Val Ser Lys Val Leu Gln
                165                 170                 175

Ile Glu Lys Glu Gly Ala Ile His Arg Glu Glu Leu Val Tyr Glu Leu
            180                 185                 190

Asn Pro Leu Asp His Arg Gly Arg Thr Leu Glu Ile Pro Gly Asn Ser
        195                 200                 205

Asp Pro Asn Met Ile Pro Asp Gly Asp Phe Asn Ser Tyr Val Arg Val
    210                 215                 220

Thr Ala Ser Asp Pro Leu Asp Thr Leu Gly Ser Glu Gly Ala Leu Ser
225                 230                 235                 240
```

-continued

```
Pro Gly Gly Val Ala Ser Leu Leu Arg Leu Pro Arg Gly Cys Gly Glu
            245                 250                 255

Gln Thr Met Ile Tyr Leu Ala Pro Thr Leu Ala Ala Ser Arg Tyr Leu
        260                 265                 270

Asp Lys Thr Glu Gln Trp Ser Thr Leu Pro Pro Glu Thr Lys Asp His
    275                 280                 285

Ala Val Asp Leu Ile Gln Lys Gly Tyr Met Arg Ile Gln Gln Phe Arg
290                 295                 300

Lys Ala Asp Gly Ser Tyr Ala Ala Trp Leu Ser Arg Asp Ser Ser Thr
305                 310                 315                 320

Trp Leu Thr Ala Phe Val Leu Lys Val Leu Ser Leu Ala Gln Glu Gln
                325                 330                 335

Val Gly Gly Ser Pro Glu Lys Leu Gln Glu Thr Ser Asn Trp Leu Leu
            340                 345                 350

Ser Gln Gln Gln Ala Asp Gly Ser Phe Gln Asp Pro Cys Pro Val Leu
        355                 360                 365

Asp Arg Ser Met Gln Gly Gly Leu Val Gly Asn Asp Glu Thr Val Ala
    370                 375                 380

Leu Thr Ala Phe Val Thr Ile Ala Leu His His Gly Leu Ala Val Phe
385                 390                 395                 400

Gln Asp Glu Gly Ala Glu Pro Leu Lys Gln Arg Val Glu Ala Ser Ile
                405                 410                 415

Ser Lys Ala Asn Ser Phe Leu Gly Glu Lys Ala Ser Ala Gly Leu Leu
            420                 425                 430

Gly Ala His Ala Ala Ala Ile Thr Ala Tyr Ala Leu Ser Leu Thr Lys
        435                 440                 445

Ala Pro Val Asp Leu Leu Gly Val Ala His Asn Asn Leu Met Ala Met
    450                 455                 460

Ala Gln Glu Thr Gly Asp Asn Leu Tyr Trp Gly Ser Val Thr Gly Ser
465                 470                 475                 480

Gln Ser Asn Ala Val Ser Pro Thr Pro Ala Pro Arg Asn Pro Ser Asp
                485                 490                 495

Pro Met Pro Gln Ala Pro Ala Leu Trp Ile Glu Thr Thr Ala Tyr Ala
            500                 505                 510

Leu Leu His Leu Leu Leu His Glu Gly Lys Ala Glu Met Ala Asp Gln
        515                 520                 525

Ala Ser Ala Trp Leu Thr Arg Gln Gly Ser Phe Gln Gly Gly Phe Arg
    530                 535                 540

Ser Thr Gln Asp Thr Val Ile Ala Leu Asp Ala Leu Ser Ala Tyr Trp
545                 550                 555                 560

Ile Ala Ser His Thr Thr Glu Glu Arg Gly Leu Asn Val Thr Leu Ser
                565                 570                 575

Ser Thr Gly Arg Asn Gly Phe Lys Ser His Ala Leu Gln Leu Asn Asn
            580                 585                 590

Arg Gln Ile Arg Gly Leu Glu Glu Glu Leu Gln Phe Ser Leu Gly Ser
        595                 600                 605

Lys Ile Asn Val Lys Val Gly Gly Asn Ser Lys Gly Thr Leu Lys Val
    610                 615                 620

Leu Arg Thr Tyr Asn Val Leu Asp Met Lys Asn Thr Thr Cys Gln Asp
625                 630                 635                 640

Leu Gln Ile Glu Val Thr Val Lys Gly His Val Glu Tyr Thr Met Glu
                645                 650                 655

Ala Asn Glu Asp Tyr Glu Asp Tyr Glu Tyr Asp Glu Leu Pro Ala Lys
```

```
                        660                 665                 670
Asp Asp Pro Asp Ala Pro Leu Gln Pro Val Thr Pro Leu Gln Leu Phe
            675                 680                 685
Glu Gly
    690

<210> SEQ ID NO 4
<211> LENGTH: 690
<212> TYPE: PRT
<213> ORGANISM: Homo sapiens

<400> SEQUENCE: 4

Ala Leu Glu Ile Leu Gln Glu Glu Asp Leu Ile Asp Glu Asp Asp Ile
1               5                   10                  15

Pro Val Arg Ser Phe Phe Pro Glu Asn Trp Leu Trp Arg Val Glu Thr
            20                  25                  30

Val Asp Arg Phe Gln Ile Leu Thr Leu Trp Leu Pro Asp Ser Leu Thr
        35                  40                  45

Thr Trp Glu Ile His Gly Leu Ser Leu Ser Lys Thr Lys Gly Leu Cys
50                  55                  60

Val Ala Thr Pro Val Gln Leu Arg Val Phe Arg Glu Phe His Leu His
65                  70                  75                  80

Leu Arg Leu Pro Met Ser Val Arg Arg Phe Glu Gln Leu Glu Leu Arg
                85                  90                  95

Pro Val Leu Tyr Asn Tyr Leu Asp Lys Asn Leu Thr Val Ser Val His
            100                 105                 110

Val Ser Pro Val Glu Gly Leu Cys Leu Ala Gly Gly Gly Gly Leu Ala
        115                 120                 125

Gln Gln Val Leu Val Pro Ala Gly Ser Ala Arg Pro Val Ala Phe Ser
130                 135                 140

Val Val Pro Thr Ala Ala Ala Val Ser Leu Lys Val Val Ala Arg Gly
145                 150                 155                 160

Gly Ser Phe Glu Phe Pro Val Gly Asp Ala Val Ser Lys Val Leu Gln
                165                 170                 175

Ile Glu Lys Glu Gly Ala Ile His Arg Glu Glu Leu Val Tyr Glu Leu
            180                 185                 190

Asn Pro Leu Asp His Arg Gly Arg Thr Leu Glu Ile Pro Gly Asn Ser
        195                 200                 205

Asp Pro Asn Met Ile Pro Asp Gly Asp Phe Asn Ser Tyr Val Arg Val
210                 215                 220

Thr Ala Ser Asp Pro Leu Asp Thr Leu Gly Ser Glu Gly Ala Leu Ser
225                 230                 235                 240

Pro Gly Gly Val Ala Ser Leu Leu Arg Leu Pro Arg Gly Cys Gly Glu
                245                 250                 255

Gln Thr Met Ile Tyr Leu Ala Pro Thr Leu Ala Ala Ser Arg Tyr Leu
            260                 265                 270

Asp Lys Thr Glu Gln Trp Ser Thr Leu Pro Pro Glu Thr Lys Asp His
        275                 280                 285

Ala Val Asp Leu Ile Gln Lys Gly Tyr Met Arg Ile Gln Gln Phe Arg
290                 295                 300

Lys Ala Asp Gly Ser Tyr Ala Ala Trp Leu Ser Arg Asp Ser Ser Thr
305                 310                 315                 320

Trp Leu Thr Ala Phe Val Leu Lys Val Leu Ser Leu Ala Gln Glu Gln
                325                 330                 335
```

Val Gly Gly Ser Pro Glu Lys Leu Gln Glu Thr Ser Asn Trp Leu Leu
            340                 345                 350

Ser Gln Gln Gln Ala Asp Gly Ser Phe Gln Asp Leu Ser Pro Val Ile
        355                 360                 365

His Arg Ser Met Gln Gly Gly Leu Val Gly Asn Asp Glu Thr Val Ala
    370                 375                 380

Leu Thr Ala Phe Val Thr Ile Ala Leu His His Gly Leu Ala Val Phe
385                 390                 395                 400

Gln Asp Glu Gly Ala Glu Pro Leu Lys Gln Arg Val Glu Ala Ser Ile
                405                 410                 415

Ser Lys Ala Asn Ser Phe Leu Gly Glu Lys Ala Ser Ala Gly Leu Leu
            420                 425                 430

Gly Ala His Ala Ala Ala Ile Thr Ala Tyr Ala Leu Ser Leu Thr Lys
        435                 440                 445

Ala Pro Val Asp Leu Leu Gly Val Ala His Asn Asn Leu Met Ala Met
    450                 455                 460

Ala Gln Glu Thr Gly Asp Asn Leu Tyr Trp Gly Ser Val Thr Gly Ser
465                 470                 475                 480

Gln Ser Asn Ala Val Ser Pro Thr Pro Ala Pro Arg Asn Pro Ser Asp
                485                 490                 495

Pro Met Pro Gln Ala Pro Ala Leu Trp Ile Glu Thr Thr Ala Tyr Ala
            500                 505                 510

Leu Leu His Leu Leu Leu His Glu Gly Lys Ala Glu Met Ala Asp Gln
        515                 520                 525

Ala Ser Ala Trp Leu Thr Arg Gln Gly Ser Phe Gln Gly Gly Phe Arg
    530                 535                 540

Ser Thr Gln Asp Thr Val Ile Ala Leu Asp Ala Leu Ser Ala Tyr Trp
545                 550                 555                 560

Ile Ala Ser His Thr Thr Glu Glu Arg Gly Leu Asn Val Thr Leu Ser
                565                 570                 575

Ser Thr Gly Arg Asn Gly Phe Lys Ser His Ala Leu Gln Leu Asn Asn
            580                 585                 590

Arg Gln Ile Arg Gly Leu Glu Glu Glu Leu Gln Phe Ser Leu Gly Ser
        595                 600                 605

Lys Ile Asn Val Lys Val Gly Gly Asn Ser Lys Gly Thr Leu Lys Val
    610                 615                 620

Leu Arg Thr Tyr Asn Val Leu Asp Met Lys Asn Thr Thr Cys Gln Asp
625                 630                 635                 640

Leu Gln Ile Glu Val Thr Val Lys Gly His Val Glu Tyr Thr Met Glu
                645                 650                 655

Ala Asn Glu Asp Tyr Glu Asp Tyr Glu Tyr Asp Glu Leu Pro Ala Lys
            660                 665                 670

Asp Asp Pro Asp Ala Pro Leu Gln Pro Val Thr Pro Leu Gln Leu Phe
        675                 680                 685

Glu Gly
    690

<210> SEQ ID NO 5
<211> LENGTH: 77
<212> TYPE: PRT
<213> ORGANISM: Homo sapiens

<400> SEQUENCE: 5

Asn Val Asn Phe Gln Lys Ala Ile Asn Glu Lys Leu Gly Gln Tyr Ala
1               5                   10                  15

-continued

```
Ser Pro Thr Ala Lys Arg Cys Cys Gln Asp Gly Val Thr Arg Leu Pro
            20              25              30

Met Met Arg Ser Cys Glu Gln Arg Ala Ala Arg Val Gln Gln Pro Asp
            35              40              45

Cys Arg Glu Pro Phe Leu Ser Cys Cys Gln Phe Ala Glu Ser Leu Arg
        50              55              60

Lys Lys Ser Arg Asp Lys Gly Gln Ala Gly Leu Gln Arg
65              70              75
```

LUNG CANCER MOLECULAR MARKERS

CROSS-REFERENCE TO RELATED APPLICATIONS

This application is the National Stage of International Patent Application No. PCT/EP2013/055823, filed Mar. 20, 2013, which claims the benefit of EP Application No. 12382113.4, filed Mar. 29, 2012, each of which is incorporated by reference in its entirety.

The present invention is generally related to diagnostic and prognostic assays. In particular, the present invention refers to the use of C4 activation fragments as diagnostic and prognostic lung cancer markers. C4 activation fragments can also be useful to estimate lung cancer risk and to decide whether a medical regimen has to be initiated and to determine whether the medical regimen initiated is efficient.

BACKGROUND ART

Lung cancer is the leading cause of cancer death worldwide. In the United States, its incidence rate is the second highest among men and women and is the most common cause of cancer death in both sexes. Similar data are found in Europe, where lung cancer is the third most common cancer and is the leading caused of cancer death. Smoking tobacco is the major risk factor for lung cancer. It is estimated that about 90% of lung cancer deaths are due to smoking.

Lung cancer comprises two main histological subtypes: small cell lung cancer (SCLC) and non-small cell lung cancer (NSCLC). The latter accounts for 80-85% of all cases and includes the two most frequent lung cancer types: adenocarcinomas and squamous cell carcinomas.

Irrespective of the histology, lung cancer is often detected at advanced stages, when the disease is almost incurable. This explains the poor five-year survival rate, which rounds 15-20% for all lung cancer tumors, and is less than 5% in metastatic cases. A lack of effective techniques for early detection is one of the main reasons behind these dismal statistics. Nowadays, less than 20% of patients are diagnosed in early stages, when surgical intervention is possible; in consequence, extensive efforts are devoted to significantly increase the percentage of early detected cases.

In the last years, low-dose circular tomography (CT)-based lung cancer screening studies have reported high rates of detection of small cancers in early stages (Henschke C. I. et al, 2006). A study including more than 50,000 participants (Aberle D. R. et al., 2011) concluded that screening with the use of spiral CT detects lung tumors at early stages (mostly stage I) and reduces mortality from lung cancer. However, to be really efficacious in population-based screening programs, high levels of sensitivity and specificity are needed. In this respect, especially interesting is the possibility of combining radiological techniques with the use of molecular markers which may select those individuals who are at higher risk of developing cancer in their lungs. Moreover, these biomarkers may help to confirm the presence of malignant cells and predict its evolution and its biological response to treatment. In particular, in CT-based lung cancer screening protocols, biomarkers may be very helpful to discriminate which of the nodules found by imaging may lead to more aggressive tumors and need more active follow up. Unfortunately, in spite of the efforts made, the search for molecular biomarkers for lung cancer has had a very limited success and, at present, there are not molecular markers available that can be routinely used for risk assessment, diagnosis, prognosis, or monitoring of treatment in lung cancer.

Some studies have suggested that the complement system is activated in patients with neoplastic diseases. In the case of lung cancer, there are contradictory results. Immunohistochemical analysis revealed a minimal deposition of C3b (a component of the alternative complement system) with an apparent lack of activation of the lytic MAC (Niehans G. A. et al., 1996). However, elevated complement levels correlating with tumor size were found in lung cancer patients (Nishioka K. et al., 1976), and complement components C3c and C4 were significantly elevated in patients with lung cancer when compared with a control group. Many proteomic studies have also reported an elevation of complement components in the plasma of lung cancer patients (Oner F. et al, 2004). It has also been disclosed that the classical complement pathway is not activated in patients suffering from lung cancer because no reduction in the levels of C4 was detected (Hou et al., 1985).

In conclusion, at present, there are not molecular markers available that can be routinely used for risk assessment, diagnosis, prognosis, or monitoring of treatment in lung cancer.

SUMMARY OF THE INVENTION

The present inventors have found that activation of the classical pathway of complement occurs in patients suffering from lung cancer. In particular, they have found that C4 activation fragments (FIG. 1), such as C4d activation fragments (C4b, iC4b and C4d, among others) and C4a, which can be detected when activation of the classical complement system occurs, are deposited in lung tissue sections from lung cancer patients (see Example 1, FIG. 2). When airway fluids or plasma samples were analyzed, C4d activation fragments were detected in a higher amount in samples from patients suffering from lung cancer than in samples from control people (see Examples 2, 3 and 4).

In addition, it has been found that C4a, which can also be detected when the activation of the classical complement pathway occurs, is found in samples from airway fluids of people suffering from lung cancer (Example 2).

Thus, in a first aspect, the present invention provides a method of diagnosis and/or prognosis of lung cancer in a subject, the method comprising the steps of:
  a) determining, in vitro, the level of a C4 activation fragment in a test sample of the subject; and
  b) comparing the level determined in step (a) with a reference control level of said C4 activation fragment, wherein if the level determined in step (a) is higher than the reference control level, it is indicative that the subject suffers from lung cancer or has a bad prognosis.

As it has been stated above, Hou et al. concluded, after analyzing serum samples from patients suffering from lung cancer with an anti-C4 antibody, that in lung cancer disease there is no differential activation of the classical pathway of complement. This affirmation was based on the fact that no change in C4 levels was detected.

Surprisingly, and contrary to the teachings of Hou et al., the present inventors have found that the classical pathway complement system is activated in patients suffering from lung cancer. This affirmation is based on the detection of high levels of C4 activation fragments, such as C4a and C4d activation fragments (which are only produced when the complement system is activated), in samples of tissue, plasma, and airway fluids of patients suffering from lung cancer.

From the experimental data included in the present application (Example 6), it can also be concluded that a C4 activation fragment can also be used as a marker for identifying a subject suspicious of suffering from lung cancer.

Therefore, in a second aspect the present invention provides a method for identifying a subject suspicious of suffering from lung cancer, the method comprising:
a) determining, in vitro, the level of a C4 activation fragment in a test sample of the subject, and
b) comparing the level of step (a) with a reference control level, wherein if the level determined in step (a) is higher than the reference control level, it is indicative that the subject is suspicious of suffering from lung cancer.

In a third aspect, the present invention provides a method of deciding or recommending whether to initiate a medical regimen of a subject suspicious of suffering lung cancer, which method comprises the steps of:
a) determining, in vitro, the level of a C4 activation fragment in a test sample of the subject; and
b) diagnosing the lung cancer or determining whether the subject is suspicious of suffering lung cancer, if the C4 activation fragment level in the test sample is higher than a reference control level of said C4 activation fragment, as defined in the method of the first or second aspect of the invention;
wherein:
i) if the subject is diagnosed of suffering from lung cancer, or of being suspicious of suffering from lung cancer, then the initiation of the medical regimen is recommended, and
ii) if the patient is diagnosed of not suffering from lung cancer, the follow-up is performed optionally in consideration of the result of an examination of the patient by a physician.

By determining the C4 activation fragment level in a test sample, the skilled person can establish, additionally, which is the most suitable therapy that can be recommended, because the level detected in the sample may reflect the extension (i.e., severity) of the disease.

Furthermore, when it is decided that a subject has to initiate a medical regimen because he suffers from, or is suspicious of having, lung cancer, it can be monitored how efficient is the regimen using C4 activation fragment as marker: a decrease or return to a normal level of C4 activation fragment (i.e., to the level of a cancer-free control subject) can indicate that the patient has reacted favourably to the medical regimen and, therefore, said regimen is effective; if the level of C4 activation fragment does not significantly change or it increases, this can indicate that the regimen is not effective. Finally, the level of C4 activation fragment can be measured after the end of the treatment for controlling relapses.

Therefore, in a fourth aspect, the present invention provides a method for determining the efficacy of a medical regimen in a patient already diagnosed of lung cancer, the method comprising the steps of:
(a) in vitro measuring the level of a C4 activation fragment in a sample from the patient prior to the administration of the medical regimen;
(b) in vitro measuring the level of said C4 activation fragment in a sample from the patient once started the administration of the medical regimen; and
(c) comparing the levels measured in steps (a) and (b), in such a way that if the C4 activation fragment level measured in step (b) is lower than the C4 activation fragment level measured in step (a), it is indicative that the medical regimen is effective in the treatment of lung cancer;
or, alternatively, the method comprising the steps of:
(i) in vitro measuring the level of a C4 activation fragment in a sample from the patient once started the administration of the medical regimen; and
(ii) comparing the level measured in step (i) with a reference control level of the C4 activation fragment, wherein, if the C4 activation fragment level measured in step (i) is not higher than the reference control level, it is indicative that the medical regimen is effective in the treatment of lung cancer.

With the method of the fourth aspect of the invention, it can be determined the treatment outcome (evaluation undertaken to assess the results or consequences of management and procedures used in combating disease in order to determine the efficacy, effectiveness, safety, practicability, etc., of these interventions in individual cases or series).

In a fifth aspect, the present invention provides the use of a C4 activation fragment as a marker for the diagnosis, prognosis or monitoring of lung cancer, or as a marker of the risk of developing lung cancer.

BRIEF DESCRIPTION OF THE DRAWINGS

In FIGS. 2 to 13, "C4d" means C4d-containing activation fragments of C4 (C4b, iC4b, and C4d, among others), which are collectively referred to as "C4d activation fragment(s)".

FIG. 3 shows the association between C4d immunostaining on lung cancer primary tissues and the clinical outcome of patients. Figures correspond to Kaplan-Meier curves for disease-free survival and lung cancer-specific survival. Patients were classified into high or low using the mean value of the C4d staining score as the cut-off. The statistical significance of the difference between groups was evaluated using the log-rank test. Dotted line: high C4d immunostaining; continuous line: low C4d immunostaining.

FIG. 4. Quantification of C4, C4d activation fragments, C4a and C5a in bronchoalveolar lavage supernatants from patients with a benign respiratory disease and patients with lung cancer. Statistical differences were analyzed with the Mann-Whitney U test. On X-axis: C=controls; T=patients with lung cancer FIG. 5. Quantification of C4, C4d activation fragments, C4a and C5a in bronchoalveolar lavage supernatants from patients with different histological subtypes of lung cancer: ADC: adenocarcinoma (n=12); SCC: squamous cell carcinoma (n=23); SCLC: small-cell lung carcinoma (n=9).

FIG. 6 corresponds to a ROC curve for the quantification of C4, C5a, C4d activation fragments and C4a in bronchoalveolar lavage supernatants from patients with a benign respiratory disease and patients with lung cancer. Values were normalized with the levels of factor H. Areas under the curve and 95% confidence intervals were: C4: 0.54 (0.39-

0.68; p=0.596); C5a: 0.48 (0.33-0.63; p=0.787); C4d: 0.77 (0.65-0.89; p<0.001); C4a: 0.67 (0.54-0.81; p=0.017).

Figure 7:
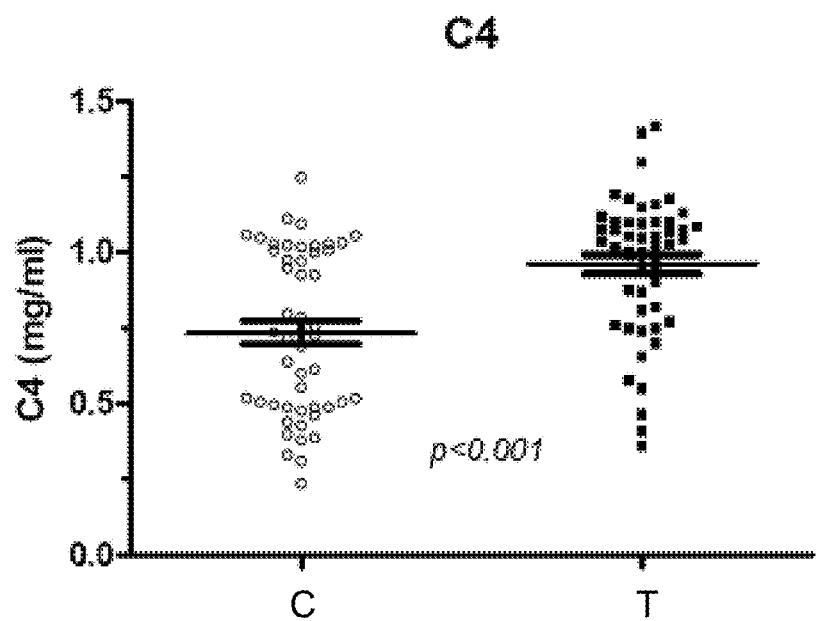
Figure 7:
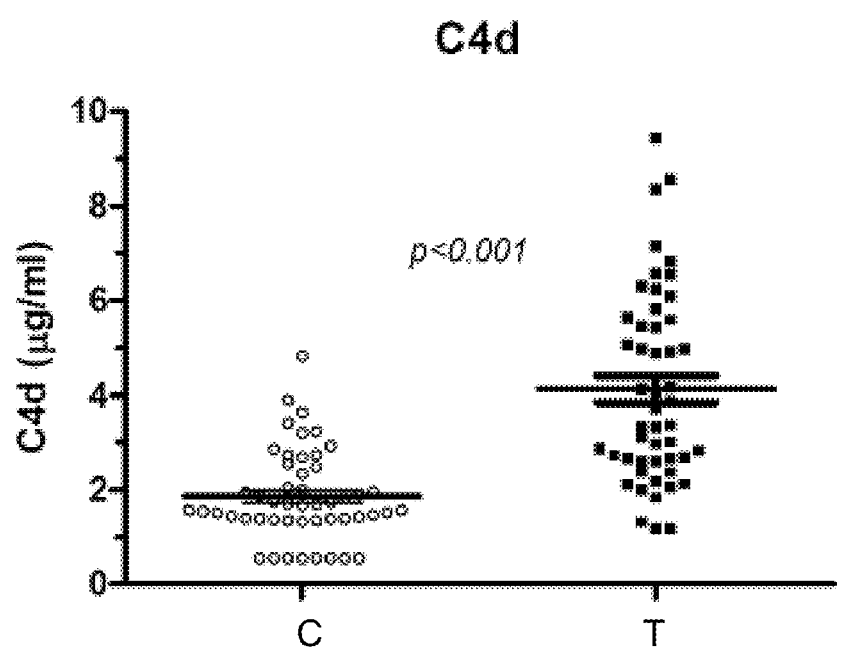

FIG. 7. Quantification of C4, C4d activation fragments, and total protein in plasma samples from healthy donors and patients with advanced lung cancer (stage IIIB and IV). Statistical differences were analyzed with the Mann-Whitney U test. On X-axis: C=healthy donors; T=advanced lung cancer patients.

Figure 8:
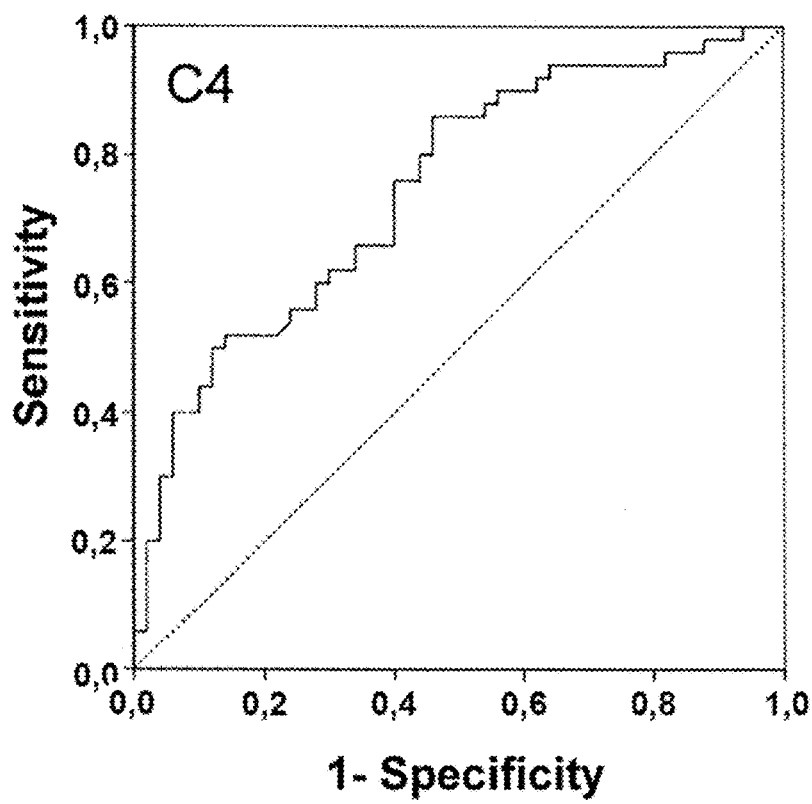
Figure 8:
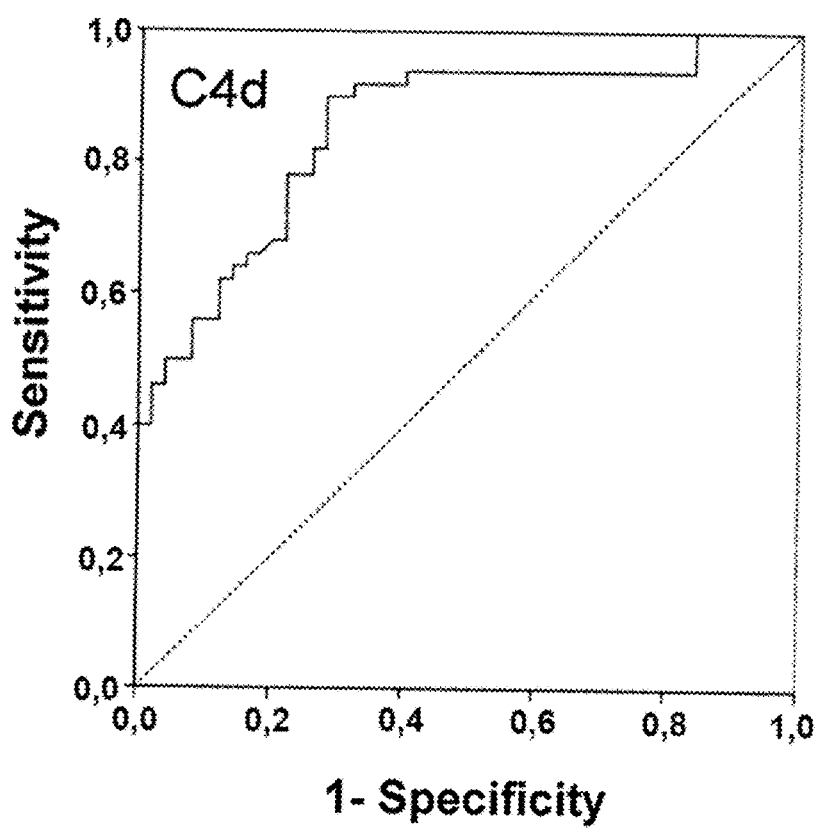
Figure 9:
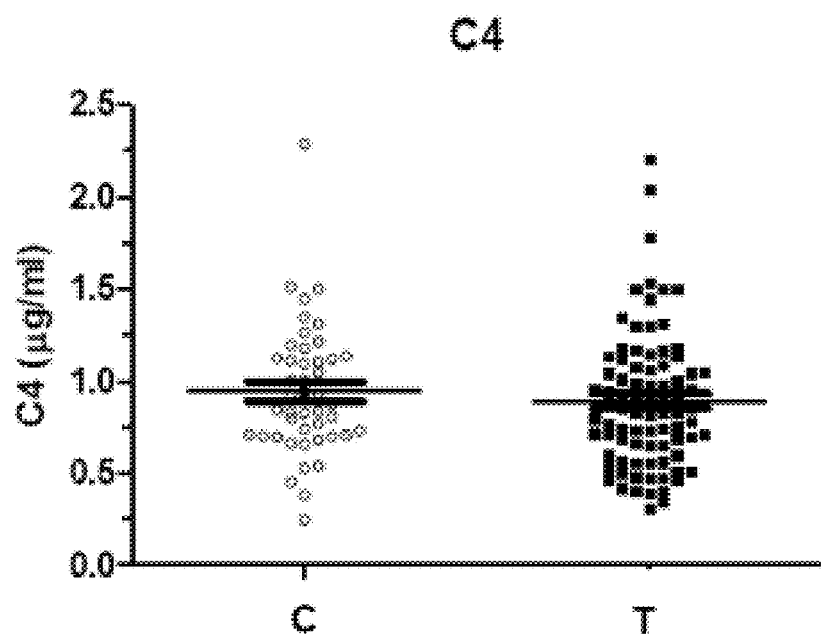
Figure 9:
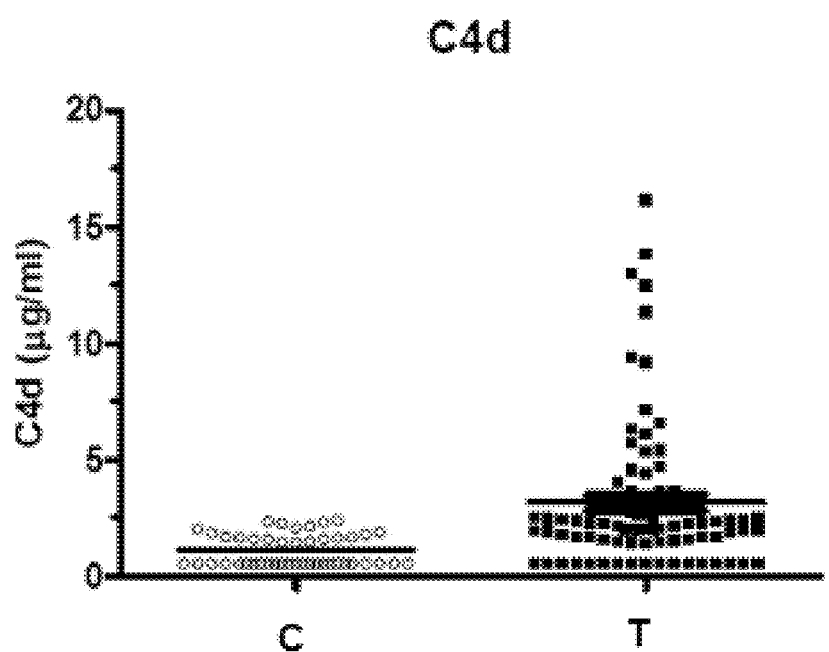

FIG. 8. ROC curve for the quantification of C4 and C4d activation fragments in plasma samples from patients with advanced lung cancer (stage IIIB and IV). Area under the curve was 0.75 (95% confidence interval, 0.65-0.84; p<0.001) for C4, and 0.86 (95% confidence interval, 0.78-0.93; p<0.001) for C4d FIG. 9 shows the quantification of C4, C4d activation fragments, and total protein in plasma samples from healthy people and patients with early stage lung cancer (stages I and II). Statistical differences were analyzed with the Mann-Whitney U test. On X-axis: C=healthy people; T=early stage lung cancer patients.

Figure 10:
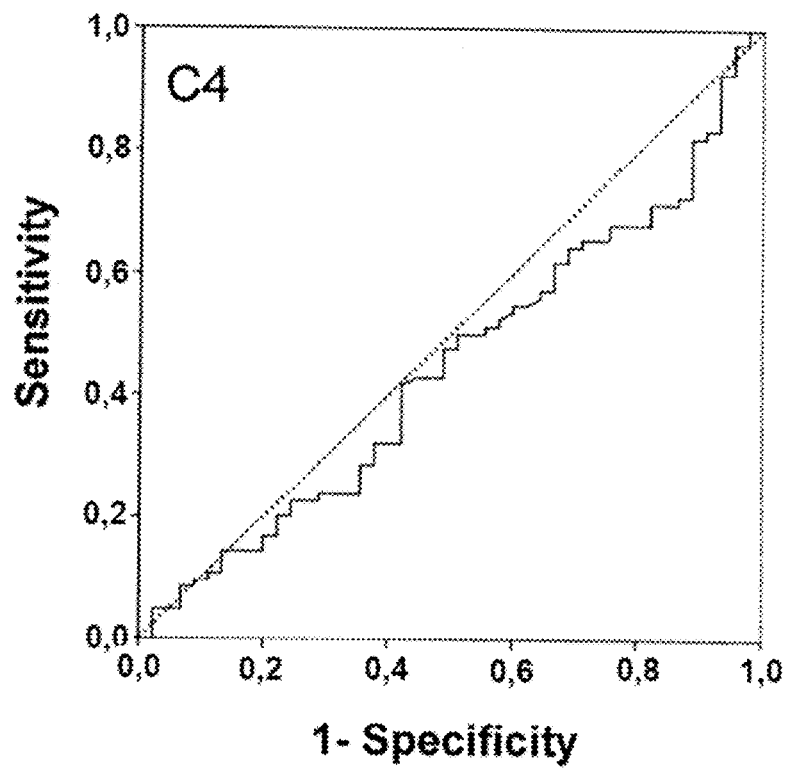
Figure 10:
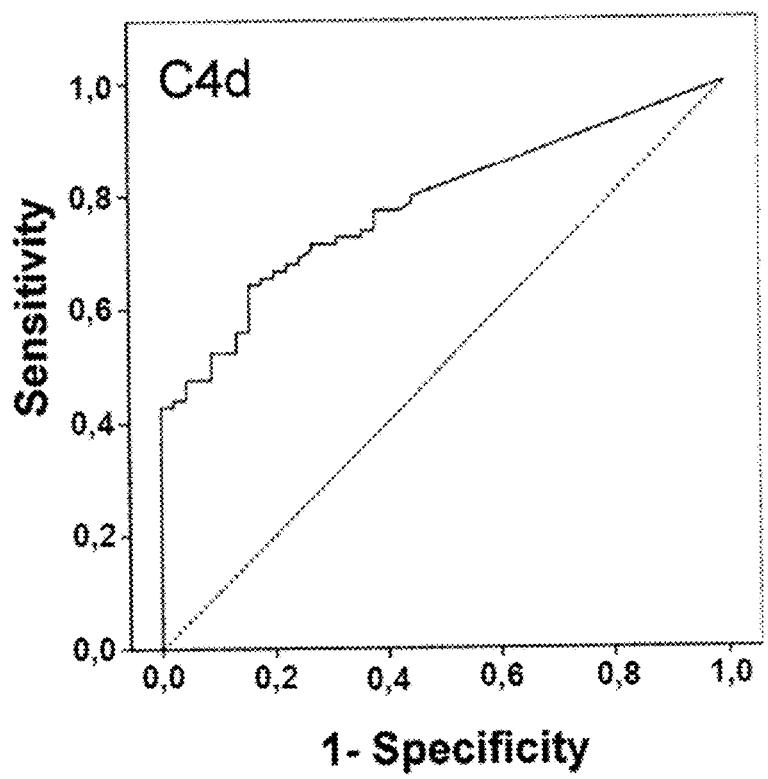

FIG. 10 corresponds to a ROC curve for the quantification of C4 and C4d activation fragments in plasma samples from patients with lung cancer in early stages (I and II). Area under the curve was 0.45 (95% confidence interval, 0.34-0.55; p=0.312) for C4, and 0.78 (95% confidence interval, 0.70-0.86; p<0.001) for C4d.

Figure 11:
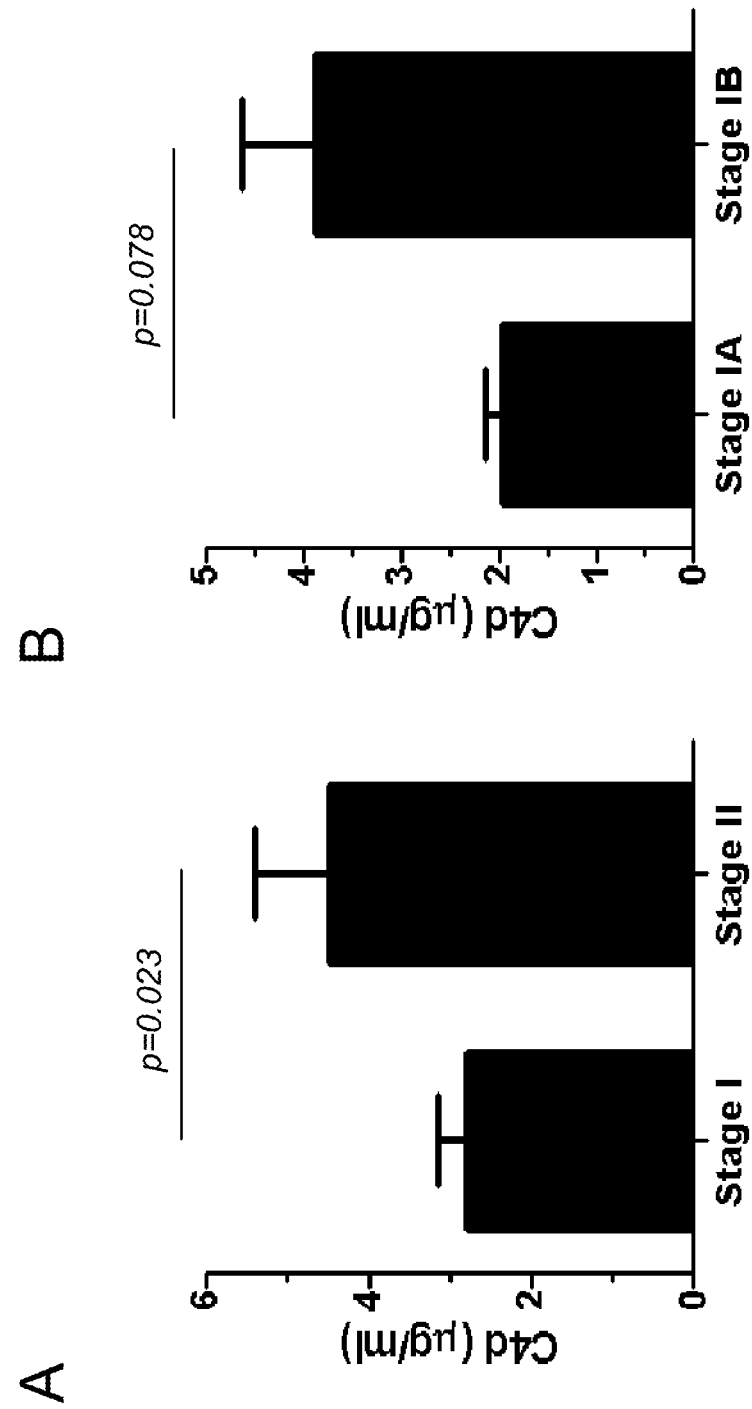

FIG. 11. Levels of C4d activation fragments in lung cancer patients separated by stage I vs. II (A) or stage IA vs. IB (B). Data represent mean±SD. Statistical differences were analyzed with the Mann-Whitney U test.

Figure 12:
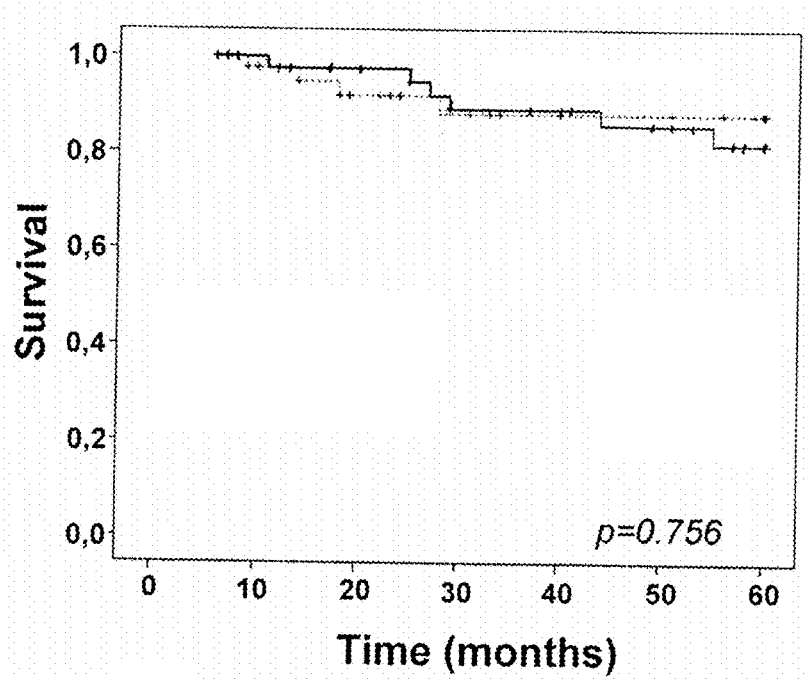
Figure 12:
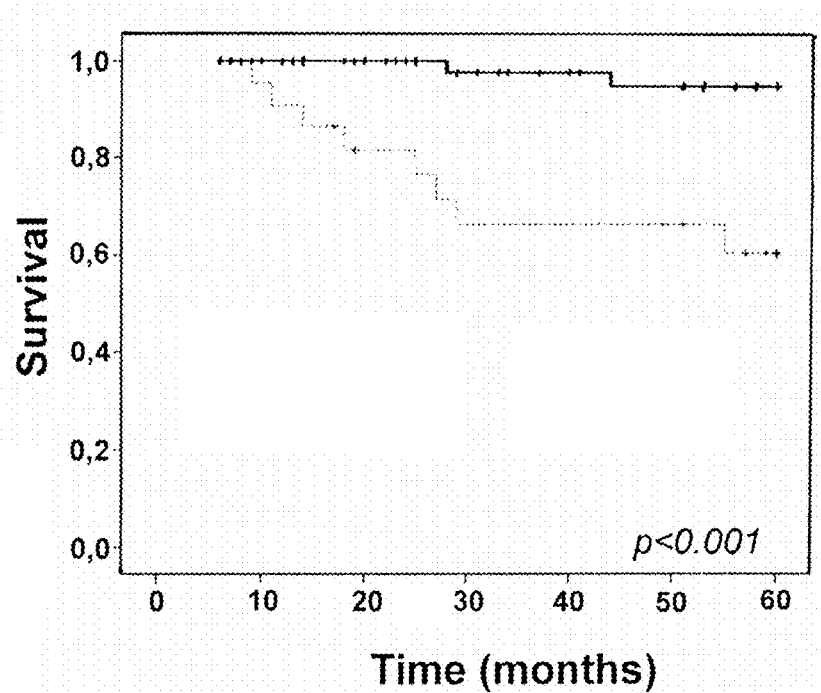

FIG. 12 shows the association between the levels C4 or C4d activation fragments in plasma and the clinical outcome of patients with lung cancer and corresponds to Kaplan-Meier curves for lung cancer-specific survival, censored at 60 months. Patients were classified into high or low using the mean value of the cohort of patients as the cut-off (3.18 μg/ml). The statistical significance of the difference between groups was evaluated using the log-rank test. Dotted line: high C4d activation fragment levels; continuous line: low C4d activation fragment levels.

Figure 13:
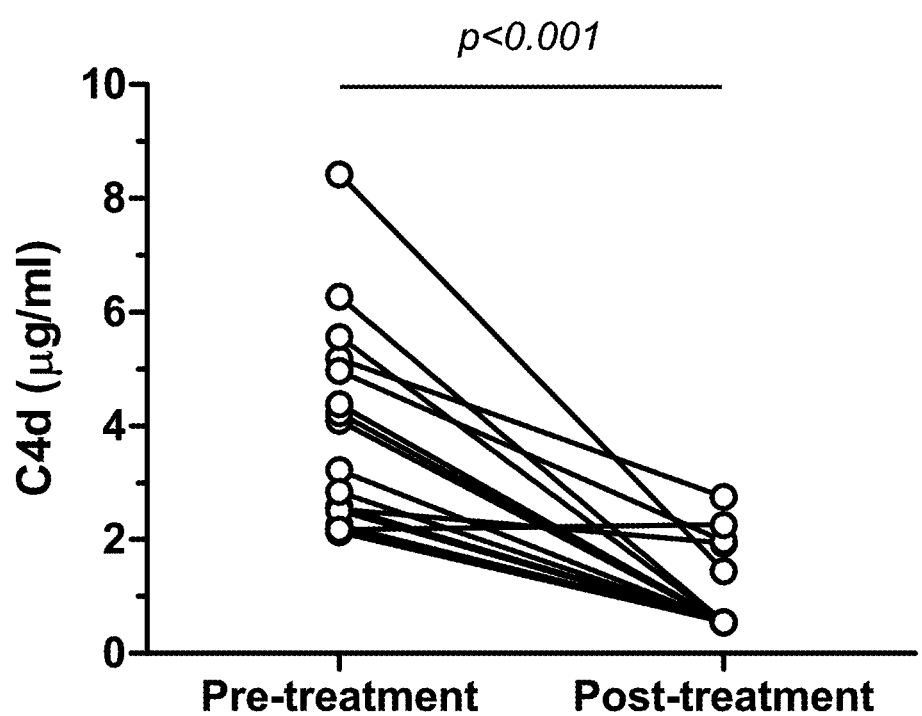

FIG. 13 shows C4d activation fragment levels in paired plasma samples from lung cancer patients obtained before and after surgical removal of the tumors (pre- and post-treatment samples, respectively). Post-treatment samples were obtained between 4 and 44 months after surgery (median: 7 months). Statistical differences were analyzed with the Wilcoxon signed-rank test.

DETAILED DESCRIPTION OF THE INVENTION

Figure 1:
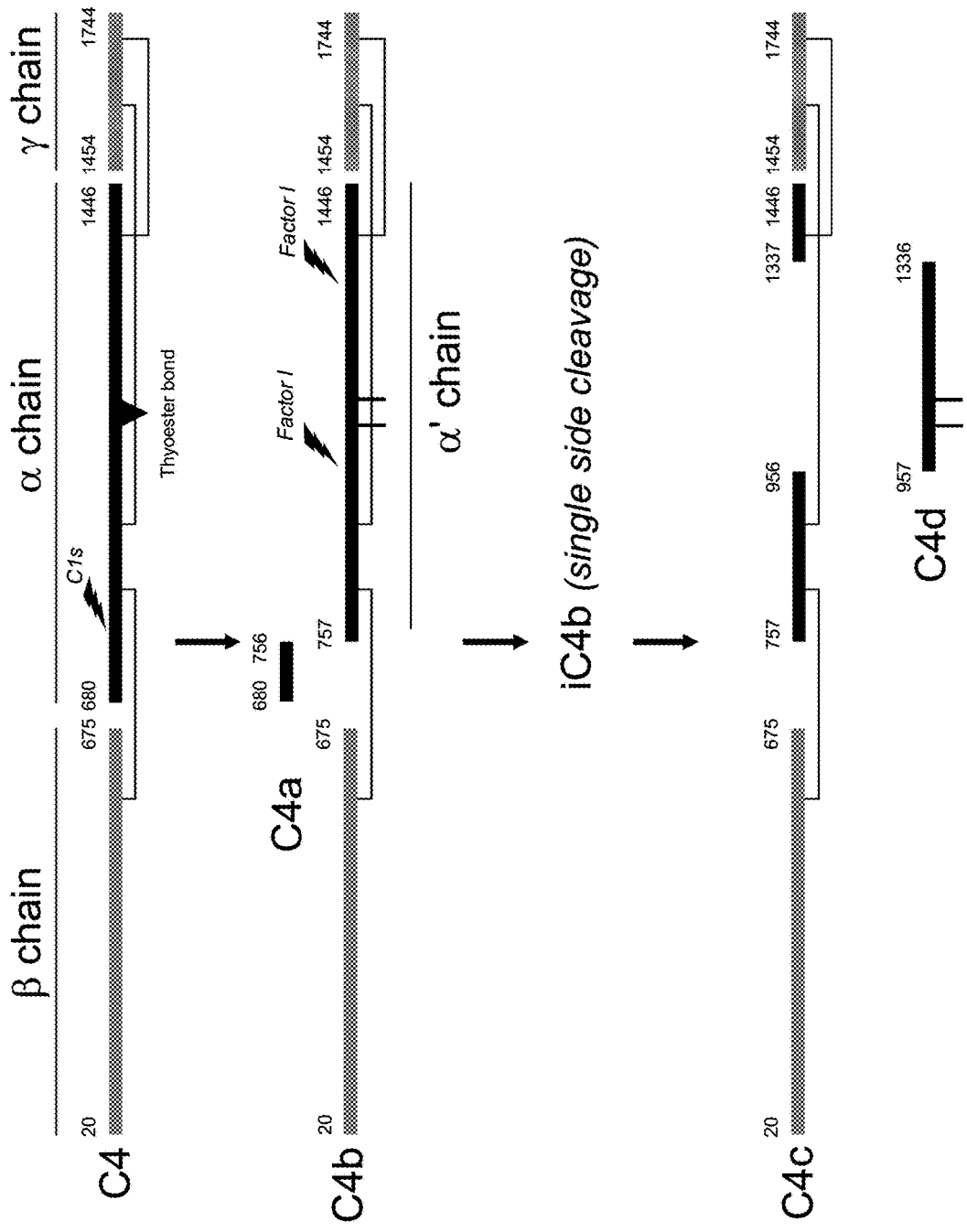
FIG. 1. Structure of the complement component C4 and its activation fragments. The numbers referred therein point out the amino acid position in respect of the full-length amino acid sequence of either of C4 isoforms (i.e., C4A or C4B). Furthermore, based on this scheme, the term "04 activation fragments" refers to all products obtained after C4 activation (C4a, C4b, iC4b, C4c and C4d among others). The term "C4d activation fragments" refers to those products obtained after C4 activation that contain C4d in their structure (C4b, iC4b, and C4d).

The present invention provides methods for the diagnosis, prognosis and for the identification of a subject suspicious of suffering lung cancer as well as methods for deciding whether to initiate a medical regimen and for determining the efficacy of the medical regimen, all based on the quantification of C4 activation fragments (FIG. 1).

In the present invention, the term "C4 activation fragment" is to be understood as encompassing any of the molecules appearing from C4 by proteolysis due to complement activation. Human genome has two genes that encode C4 protein isoforms "Complement C4-A" (Uniprot accesion number: POCOL4, Version 78) and "Complement C4-B" (Uniprot accession number: POCOL5, Version 78), briefly referred to as C4A and C4B. Thus, the expression "C4 activation fragment" encompasses the fragments due to the proteolysis from either C4A or C4B isoforms. Preferably, the C4 activation fragment is selected from the group consisting of: C4a, C4d activation fragments, and combinations thereof.

In the present invention, the expression "C4d activation fragment" is to be understood as encompassing any of the molecules appearing from C4 by proteolysis, with the proviso that said molecule(s) include(s) either SEQ ID NO: 1 or SEQ ID NO: 2 (hereinafter also referred as "C4d sequences"). Although C4 is a molecule that includes C4d sequence, it is an inactive precursor; therefore the term "C4d activation fragment" does not embrace C4. SEQ ID NO: 1 corresponds to the C4d sequence from C4A ((Uniprot accesion number: POCOL4, Version 78) and corresponds to the amino acid residues 957-1336 of said isoform. SEQ ID NO: 2 corresponds to the C4d sequence from C4B (Uniprot accession number: POCOL5, Version 78) and corresponds to the amino acid residues 957-1336 of said isoform. The molecules that appear when activation of complement occurs and which comprise either SEQ ID NO: 1 or SEQ ID NO: 2 are, among others, C4b, iC4b and C4d. Thus, when the methods of the first, second, third and fourth aspects, as well as the use of the fifth aspect, refer to "C4d activation fragment", they encompass the determination of C4b, iC4b, C4d or a combination thereof. The expression "combination thereof" encompasses the determination of C4d+C4b, C4d+iC4b, C4b+iC4b and C4d+C4b+iC4b. In a preferred embodiment, "C4d activation fragment" corresponds to the combination C4d+C4b+iC4b.

C4b differs from the sequence and conformational structure of C4 (either of C4A or C4B isoforms) in the alpha chain, wherein a proteolysis occurs. Proteolysis takes place between amino acids 756-757, producing C4b and a small fragment known as C4a. Thus, the alpha chain of C4b is either SEQ ID NO: 3 or 4, depending of the gene from which is produced. The other two chains (beta and gamma) are identical to those of C4.

iC4b differs from C4b by a proteolysis cleavage between either amino acids 956-957 or 1336-1337. When both proteolysis cleavages take place, C4c and C4d activation fragments are produced, wherein C4d consists of any one of the two "C4d sequences" mentioned above.

The term "diagnosis" is known to the person skilled in the art. As used herein "diagnosis" is understood as becoming aware of a particular medical condition, syndrome, complication or risk in a subject; the determination of the nature of the disease or condition; or the distinguishing of one disease or condition from another. It refers both to the process of attempting to determine or identify the possible disease or disorder, and to the opinion reached by this process. A diagnosis, in the sense of diagnostic procedure, can be regarded as an attempt at classification of an individual's condition into separate and distinct categories that allow medical decisions about treatment and prognosis to be made. Subsequently, a diagnostic opinion is often described in terms of a disease or other condition. However, a diagnosis can take many forms. It might be a matter of detecting the presence and naming the disease, lesion, dysfunction or disability. It might be an exercise to attribute a category for management or for prognosis. It may indicate either degree of abnormality on a continuum or kind of abnormality in a classification.

The in vitro diagnostic method of the first aspect of the invention can be performed with a sample of: (a) an asymptomatic subject, (b) a subject which has already been identified as being suspicious of suffering from lung cancer, (c) a subject already diagnosed of lung cancer, as complementary confirmation diagnostic assay or (d) a subject with high risk of suffering the disease. In order to determine whether a subject has a high risk of suffering lung cancer it has to determine whether he complies with one or more of the following criteria: (a) smoking; (b) environmental factors, such as exposure to toxic substances or carcinogens (secondhand smoke, asbestos, arsenic, sulfur, particulate matter, radioisotopes, ionizing radiation, nickel, chromium, and other metals can increase the risk of lung cancer), (c) age; (d) viral infections (for instance, human papillomavirus, JC virus, simian virus 40, BK virus, or cytomegalovirus); (e) family history (e.g. anyone with a first-degree relative—parent, brother, sister—with lung cancer has a higher risk of developing lung cancer); and (f) genetic risk (inherited genetic variants associated with predisposition to lung cancer).

"Prognosis" as used herein refers to the prediction of the probable progression and outcome of a disease. It includes: neoplasm grading (attempt to express in replicable terms the level of cell differentiation in neoplasms as increasing anaplasia correlates with the aggressiveness of the neoplasm), neoplasm staging (attempt to express in replicable terms the extent of the neoplasm in the patient).

In the present invention, the term "reference control level" referred to in the methods of the first, second, third, and fourth aspect is to be understood as a predefined value of a given molecular marker, a C4 activation fragment in the present case, which is derived from the levels of said molecular marker in a sample or group of samples. The samples are taken from a subject or group of subjects wherein the presence, absence, stage, or course of the disease has been properly performed previously. This value is used as a threshold to discriminate subjects wherein the condition to be analyzed is present from those wherein such condition is absent (i.e. subject having lung cancer from subjects free of lung cancer), to determine the stage of the disease, the risk of developing or of being suffering from lung cancer, among others. This reference control level is also useful for determining whether the subject has to initiate a medical regimen and how effective the regimen is. The subject or subjects from whom the "reference control level" is derived may include subject/s wherein the condition is absent, subject/s wherein the condition is present, or both. The skilled person in the art, making use of the general knowledge, is able to choose the subject or group of subjects more adequate for obtaining the reference control level for each of the methods of the present invention.

Methods for obtaining the reference value from the group of subjects selected are well-known in the state of the art (Burtis C. A. et al., 2008, Chapter 14, section "Statistical Treatment of Reference Values") In a particular case "reference control level" is a cut-off value defined by means of a conventional ROC analysis (Receiver Operating Characteristic analysis). As the skill person will appreciate, optimal cut-off value will be defined according to the particular applications of the diagnostic or prognostic method: purpose, target population for the diagnosis or prognosis, balance between specificity and sensibility, etc.

In a preferred embodiment, when performing the method for determining the risk for developing lung cancer provided in the present application, the control subjects are selected on the basis of being asymptomatic people with a risk for developing the disease due to one or more of the following criteria: (a) smoking; (b) environmental factors, such as exposure to toxic substances or carcinogens (secondhand smoke, asbestos, arsenic, sulfur, particulate matter, radioisotopes, ionizing radiation, nickel, chromium, and other metals can increase the risk of lung cancer), (c) age; (d) viral infections (for instance, human papillomavirus, JC virus, simian virus 40, BK virus, or cytomegalovirus); (e) family history (e.g. anyone with a first-degree relative—parent, brother, sister—with lung cancer has a higher risk of developing lung cancer); and (f) genetic risk (inherited genetic variants associated with predisposition to lung cancer).

In a preferred embodiment of the method of the first, second, third and fourth aspects of the invention, as well as the use of the fifth aspect, the molecule to be detected in step (a) is a C4d activation fragment.

Figure 3:
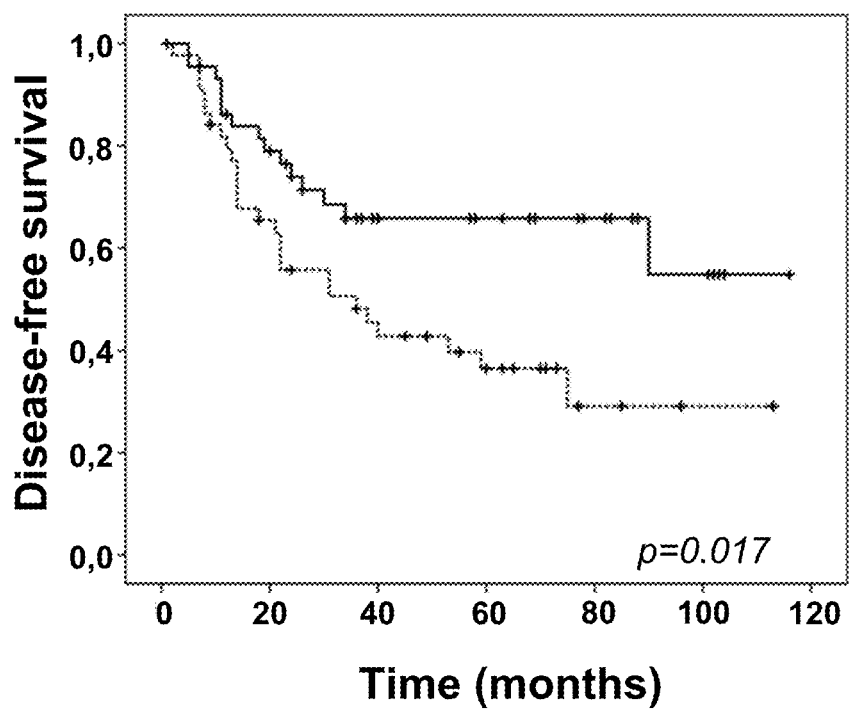
Figure 3:
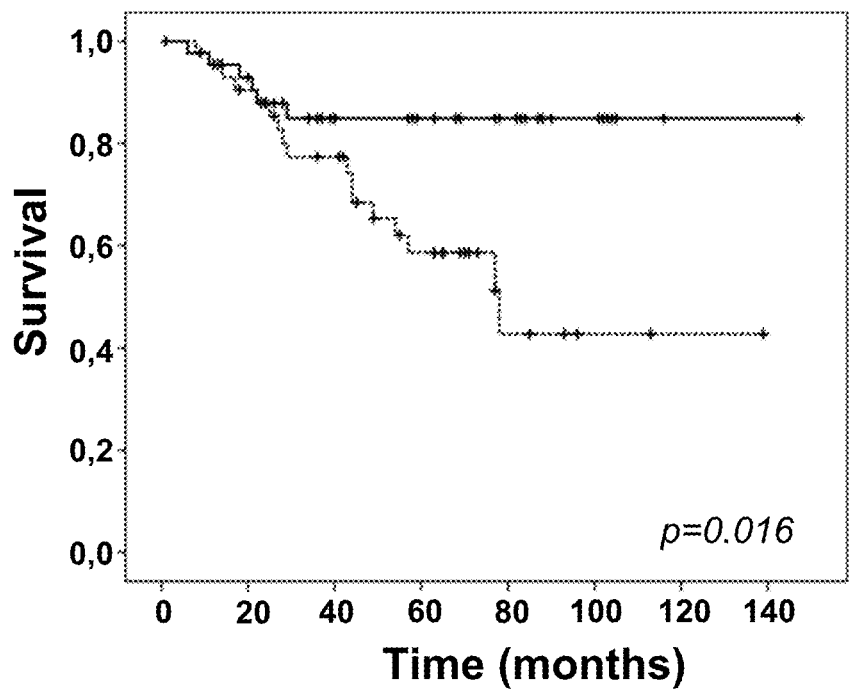

It has been found that the level of C4d activation fragments detected in the sample reflects the severity of the disease: the higher the level of the marker is detected, the worse is the prognosis of the disease (FIG. 3 and FIG. 9).

Thus, in an embodiment the present invention provides a method of diagnosis and/or prognosis of lung cancer in a subject, the method comprising the steps of:

a) determining, in vitro, the level of a C4d activation fragment in a test sample of the subject; and b) comparing the level determined in step (a) with a reference control level of said C4d activation fragment, wherein if the level determined in step (a) is higher than the reference control level, it is indicative that the subject suffers from lung cancer or has a bad prognosis.

Figure 6:
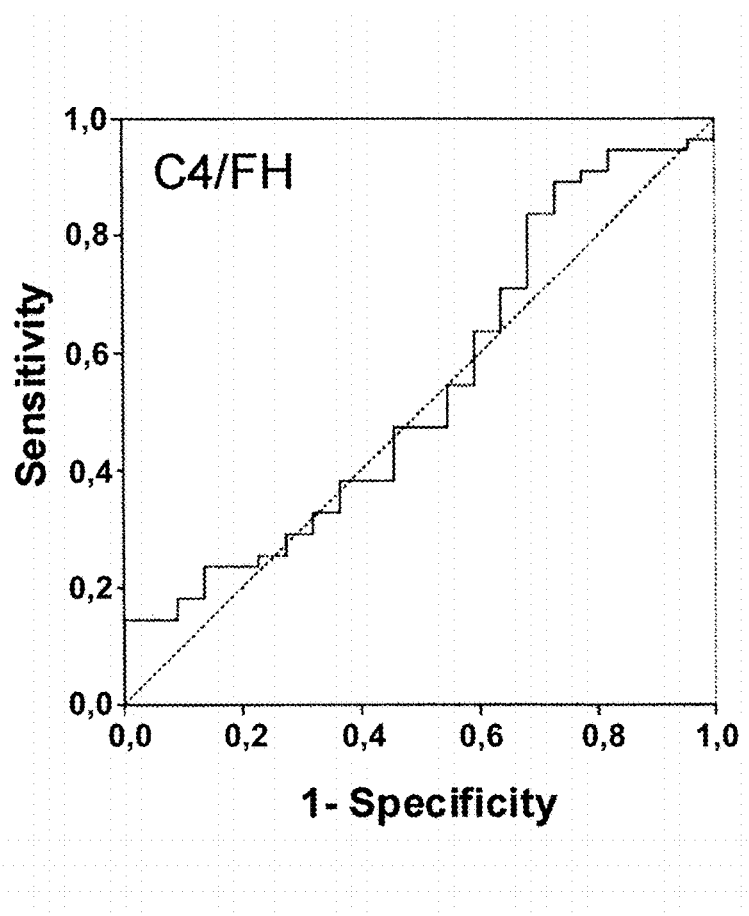
Figure 6:
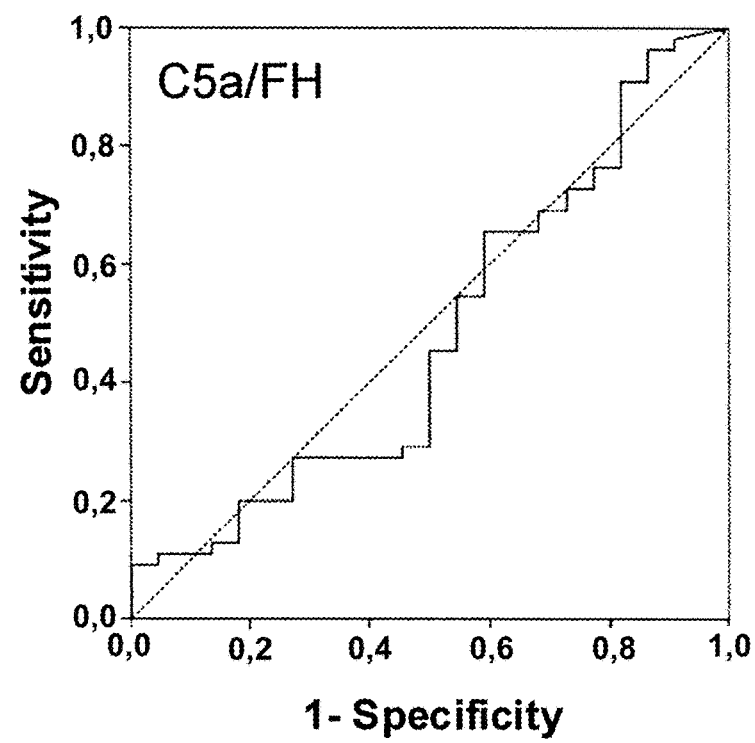

It has been found that C4d activation fragment allows the discrimination between controls and patients suffering from lung cancer with high sensitivity and specificity (Examples 2, 3 and 4, FIGS. 6, 8 and 10). This confers to the method of the first aspect of the invention the ability to discriminate between healthy and sick individuals, reducing the detection of false positives associated with other diagnostic methods based on the detection of other molecular markers or the detection of suspected nodules by imaging techniques such as the CT-scanning.

Furthermore, it has been found that C4d activation fragments are present at high concentrations in lung cancer patients compared with healthy controls in an early stage (Example 4). As it has been stated above, lung cancer is often detected at advanced stages, when the disease is almost incurable. With the method of the present invention, the diagnosis could be performed in an early stage (because the level of C4d activation fragments is high enough to be detected), being possible the surgical intervention of the patient at an early stage. Consequently, using the method of the first aspect of the invention, the survival-rate of patients diagnosed of lung cancer would be improved.

Furthermore, some of the examples included in the present application show the valuable information provided by C4d activation fragment as lung cancer biomarkers when compared with C4. These assays were performed in order to determine whether C4d activation fragments, which appears in plasma when classical pathway complement activation occurs, provides different information about lung cancer disease when compared with C4. As it is shown in Examples 2, 3, and 4, determination of C4d activation fragment is more selective and specific than determination of C4 when their diagnostic values are analyzed. In addition, Example 5 illustrates that C4 is not useful as a biomarker to provide information about the clinical outcome of the disease, on the contrary of C4d activation fragment, which can provide this useful information.

From the experimental data included in the present application (Example 6), it can be concluded that C4d activation fragments can also be used as a marker for identifying subjects suspicious of suffering lung cancer.

Therefore, in a preferred embodiment the present invention provides a method for identifying a subject suspicious of suffering from lung cancer, the method comprising:
a) determining, in vitro, the level of a C4d activation fragment in a test sample of the subject, and
b) comparing the level of step (a) with a reference control level, wherein if the level determined in step (a) is higher than the reference control level, it is indicative that the subject is suspicious of suffering from lung cancer.

In a preferred embodiment, the present invention provides a method of deciding or recommending whether to initiate a medical regimen of a subject suspicious of suffering lung cancer, which method comprises the steps of:
a) determining, in vitro, the level of a C4d activation fragment in a test sample of the subject; and
b) diagnosing the lung cancer or determining whether the subject is suspicious of suffering lung cancer, if the C4d activation fragment level in the test sample is higher than a reference control level of said C4d activation fragment, as defined above;
wherein:
i) if the subject is diagnosed of suffering from lung cancer, or of being suspicious of suffering from lung cancer, then the initiation of the medical regimen is recommended, and
ii) if the patient is diagnosed of not suffering from lung cancer, the follow-up is performed optionally in consideration of the result of an examination of the patient by a physician.

By determining the C4d activation fragment level in a test sample, the skilled person can establish, additionally, which is the most suitable therapy that can be recommended, because the level detected in the sample may reflect the extension (i.e., severity) of the disease.

Furthermore, once it has decided to initiate the medical regimen because the subject is suffering from lung cancer, it can be monitored how efficient is the regimen: a decrease or return to a normal level of C4d activation fragment (i.e., to the level of a healthy subject) can indicate that the patient has reacted favourably to the medical regimen and, therefore, said regimen is effective; if the level of C4d activation fragment does not significantly change or it increases, this can indicate that the regimen is not effective. Finally, the level of C4d level can be measured at the end of the treatment for controlling relapses.

Therefore, in an embodiment the present invention provides a method for determining the efficacy of a medical regimen in a patient already diagnosed of lung cancer, the method comprising the steps of:
(a) in vitro measuring the level of a C4d activation fragment in a sample from the patient prior to the administration of the medical regimen;
(b) in vitro measuring the level of said C4d activation fragment in a sample from the patient once started the administration of the medical regimen; and
(c) comparing the level measured in steps (a) and (b), in such a way that if the C4d activation fragment level measured in step (b) is lower than the C4d activation fragment level measured in step (a), it is indicative that the medical regimen is effective in the treatment of lung cancer;
or, alternatively, the method comprising the steps of:
(i) in vitro measuring the level of a C4d activation fragment in a sample from the patient once started the administration of the medical regimen; and
(ii) comparing the level measured in step (i) with a reference control level of the C4d activation fragment,
wherein, if the C4d activation fragment amount measured in step (i) is not higher than the reference control level, it is indicative that the medical regimen is effective in the treatment of lung cancer.

In a fifth aspect, the present invention provides the use of C4d activation fragments as a marker for the diagnosis, prognosis of lung cancer, or as a marker for monitoring lung cancer.

In a preferred embodiment of the method of the first aspect of the invention as well as the use of the fifth aspect, the molecule to be detected in step (a) is C4a.

The term "C4a" refers to the 77 amino acid fragment generated by proteolysis between amino acids 756-757 of the alpha chain of C4 sequence (either from C4A or C4B) and corresponds to SEQ ID NO: 5.

Thus, in an embodiment the present invention provides a method of diagnosis and/or prognosis of lung cancer in a subject, the method comprising the steps of:
a) determining, in vitro, the level of C4a in a test sample of the subject; and
b) comparing the level of step (a) with a reference control level of said C4a,
wherein if the level of C4a is higher than the reference control level, it is indicative that the subject suffers from lung cancer or has a bad prognosis.

Preferably, the methods of the invention are immunoassay methods. More preferably the immunoassay method is an ELISA (enzyme-linked immunosorbent assay) or RIA (radioimmunoassay).

An immunoassay is a specific type of biochemical test that measures the presence or concentration of a substance (referred to as the "analyte") in solutions that frequently contain a complex mixture of substances. This type of reaction involves the binding of one type of molecule, the antigen, with a second type, the antibody. Immunoassays can be carried out using either the antigen or the antibody in order to test for the other member of the antigen/antibody pair.

In an embodiment, in order to carry out the protein detection in the methods of the present invention, antibodies or fragments thereof with the ability of binding to C4d activation fragments can be used.

In the present invention, the term "antibody or a fragment thereof with the ability of binding to C4d activation fragments" is to be understood as any immunoglobulin or fragment thereof able to selectively bind the antigen defined by SEQ ID NO: 1 or SEQ ID NO: 2. It includes monoclonal and polyclonal antibodies. The term "fragment thereof" encompasses any part of an antibody having the size and conformation suitable to bind an epitope of C4d. Suitable fragments include F(ab), F(ab') and Fv. An "epitope" is the part of the antigen being recognized by the immune system (B-cells, T-cells or antibodies).

When performing any of the methods of the present invention, the skilled person can choose how to proceed when selecting the antibodies. For instance, the skilled person can opt to select a single antibody or several antibodies. In case that the skilled person opted by a single antibody for combined detection of C4d+C4b+iC4b, it should have the ability of binding to one epitope of SEQ ID NO: 1 or SEQ ID NO: 2, said epitope being common to all C4d, C4b and iC4b. In case that the skilled person opted by several antibodies, they should have the ability of binding to different epitopes of SEQ ID NO: 1 or SEQ ID NO: 2.

The antibody or fragment thereof for detecting C4d activation fragments can be included in a kit. The kit may additionally comprise means (additives, solvents) to visualize the antigen-antibody interactions (dipsticks, chemiluminescent reagents, turbidimetric reagents, etc.). Although the assays performed in the Examples below have been made with one kit including a single capture antibody able to bind all C4d, C4b and iC4b, the invention can be performed with any other antibody or combination of antibodies, provided that they recognize epitopes of SEQ ID NO: 1 or SEQ ID NO: 2.

In another embodiment, in order to carry out the protein detection in the methods of the present invention, antibodies or fragments thereof with the ability of binding to C4a can be used.

In the present invention, the term "antibody or a fragment thereof with the ability of binding to C4a" is to be understood as any immunoglobulin or fragment thereof able to selectively bind the antigen defined by C4a. It includes monoclonal and polyclonal antibodies. The term "fragment thereof" encompasses any part of an antibody having the size and conformation suitable to bind an epitope of C4a. Suitable fragments include F(ab), F(ab') and Fv. An "epitope" is the part of the antigen being recognized by the immune system (B-cells, T-cells or antibodies).

The antibody or fragment thereof for detecting C4a can be included in a kit. The kit may additionally comprise means (additives, solvents) to visualize the antigen-antibody interactions (dipsticks, chemiluminescent reagents, turbidimetric reagents, etc.).

In a preferred embodiment, the test sample is selected from the group consisting of: plasma, serum, bronchoalveolar lavage fluid, sputum, biopsy and surgical specimens.

In another preferred embodiment, the control sample is selected from the group consisting of: plasma, serum, bronchoalveolar lavage fluid, sputum, biopsy and surgical specimens.

The sample extracted from the patient, as well as from the control, can be a portion of lung tissue extracted by biopsy or surgery (using routine techniques for a person skilled in the art), or a sample of peripheral fluid such as plasma, serum, bronchoalveolar lavage fluid or sputum, amongst others. As it is shown below, in Examples 2-3, C4d activation fragments are differentially detected in bronchoalveolar lavage fluid and plasma of lung cancer patients, with the highest sensitivity and specificity. The possibility of diagnosing lung cancer from a sample of plasma or bronchoalveolar lavage fluid with high sensitivity and specificity confers an additional advantage to the method of the first aspect of the invention, since this would avoid having to resort to tissue biopsies (which, being invasive techniques, can give rise to post-surgical complications in individuals with certain profiles). Moreover, the analysis of bronchoalveolar lavage fluid or plasma can be incorporated into early detection protocols based on imaging methods.

In the present invention, the expression "medical regimen" is to be understood as encompassing either pharmacological therapies (such as chemotherapy and radiotherapy) as well as other clinical decisions taken by a physician (such as surgery in order to extirpate the part of the lung affected by the disease), among others.

In the present invention, the expression "optionally in consideration of the result of an examination of the patient by a physician" concerning the method of the fourth aspect of the invention, encompasses any clinical examination test useful in providing evidence of lung condition.

In a preferred embodiment, the lung cancer is selected from the group consisting of: non-small cell lung cancer and small-cell lung carcinoma.

Throughout the description and claims the word "comprise" and variations of the word, are not intended to exclude other technical features, additives, components, or steps. Furthermore, the word "comprise" and its variations encompasses the term "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1. The Classical Complement Pathway is Activated on Lung Primary Tumors

Description of the Experiment

Activation of the classical pathway of complement by lung primary tumors was evaluated by the assessment of C4d activation fragment deposition on tumor cells.

Material and Methods

Resected primary lung tumors, from patients recruited at the Clinica Universidad de Navarra, were fixed in formalin and embedded in paraffin. The study protocol was approved by the Institutional Ethical Committee, and all patients gave written informed consent. A tissue microarray set was constructed and used for the immunohistochemical detection of C4d activation fragments as follows. After paraffin removal and endogenous peroxidase inhibition (3% $H_2O_2$, 10 min), sections were incubated overnight at 4° C. with a rabbit polyclonal anti-human C4d antibody (BI-RC4d, Biomedica) diluted at 1:50 in REAL antibody diluent (52022, Dako), followed by detection with the Envision system (K4011, Dako). Sections were washed, lightly counterstained with hematoxylin (HX080645, Merck), dehydrated, and mounted in p-xylene-bis-pyridinium bromide (360294, BHD). Quantification of C4d activation fragment immunostaining was carried out by two observers who were unaware of the clinical features and outcome of patients. The extension of staining was scored as the percentage of positive cells (0-100%), and the intensity was assessed by comparison with a known external positive control (0, below the level of detection; 1, weak; 2, moderate; and 3, strong). Scores were calculated by multiplying the staining intensity and extension at each intensity level.

Results

Figure 2:
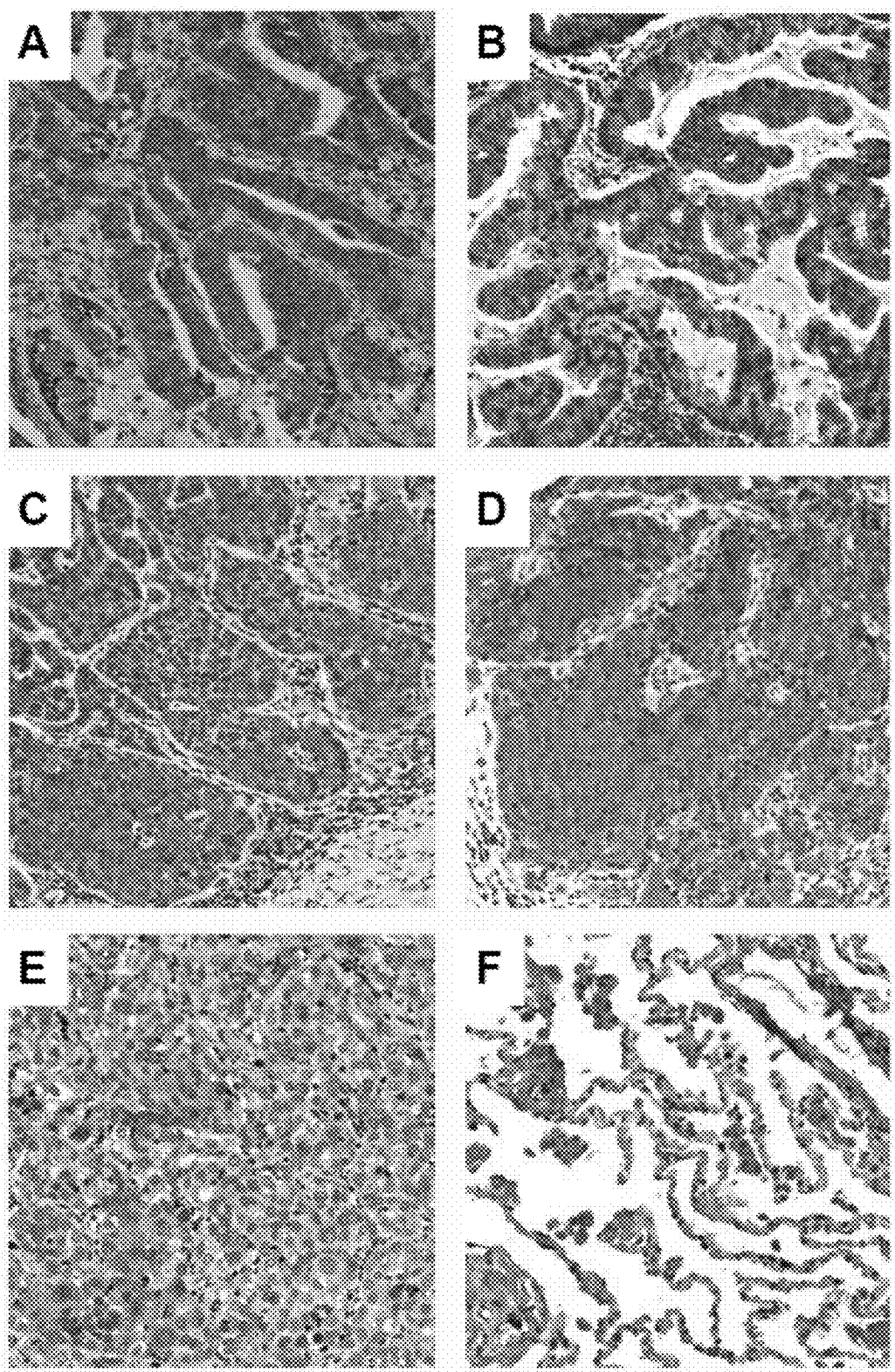
FIG. 2. Representative immunostainings for C4d deposition in lung cancer specimens (A-E) and in normal lung epithelium (F).

Deposition of C4d activation fragments on lung primary tumors was evaluated by immunocytochemistry to assess the activation of the classical pathway of complement. According to the manufacturer's specifications, the antibody used for this technique was able to recognize any of the fragments originated from C4 after its activation: C4b, iC4d and/or C4d (FIG. 1). Cytoplasmic staining was found in most tumors. In some of them, C4d staining was also apparent in the cell membrane. Normal epithelium did not show deposition of these complement fragments. FIG. 2 shows the positive result for the immunolocalization of C4d activation fragments in some representative lung tumor sections (FIGS. 2 A to E). It also illustrates the absence of staining in normal alveolar epithelium (FIG. 2F).

The clinical outcome of the patients was compared with the levels of C4d activation fragment staining (FIG. 3). High levels of C4d activation fragments were significantly associated with earlier progression and worse lung cancer-specific survival (p=0.017 and p=0.016, respectively).

This result supports the fact that primary lung tumors are able to activate the classical complement pathway and that this activation is associated with worse prognosis.

Example 2. C4 Activation Fragments are Increased in Bronchoalveolar Lavage Fluids from Lung Cancer Patients Material and Methods Seventy eight subjects undergoing diagnostic bronchoscopy at the Clinica Universidad de Navarra were consecutively included in the study. Bronchoscopy and sample collection was performed as previously described (Pio R. et al., 2010). Lung tumors were classified according to the World Health Organization 2004 classification (Travis W. D. et al., 2004). The study protocol was approved by the Institutional Ethical Committee, and all patients gave written informed consent. Bronchoalveolar lavage samples were divided into two groups: samples from patients with non-malignant lung diseases (control group; n=22) and samples from patients with lung malignancies (tumor group; n=55). The benign pulmonary diseases in the control group and the histologies in the lung cancer group have been already described (Pio R. et al., 2010). Samples were stored at −80° C. until analysis.

For marker determination, samples were spun down at 300 g for 10 min, and the supernatants were collected. Commercially-available enzyme-linked immunosorbent assays (ELISA) were used for the determinations of C4 (EC3202-1, Assaypro), C4d activation fragments (A008, Quidel), C4a (550947, BD) and C5a (DY2037, R&D). Samples were diluted 1:1000 for C4; 1:10 for C4d, 1:250 for C4a, and 1:100 for C5a. Samples below the quantification limit of the kit were assigned a concentration of one-half of the quantification limit.

The kit used for detecting C4d activation fragments, according to manufacturer's instructions, is able to detect C4b, C4d and iC4b.

Results

The fact that the classical complement pathway is activated on primary lung tumors does not imply that factors of complement activation can be released from the tumor microenvironment and be found in patient's biological fluids. To test this possibility, activation of the classical complement pathway was evaluated on airway fluids from lung cancer patients and from patients with non-malignant diseases.

Figure 4:
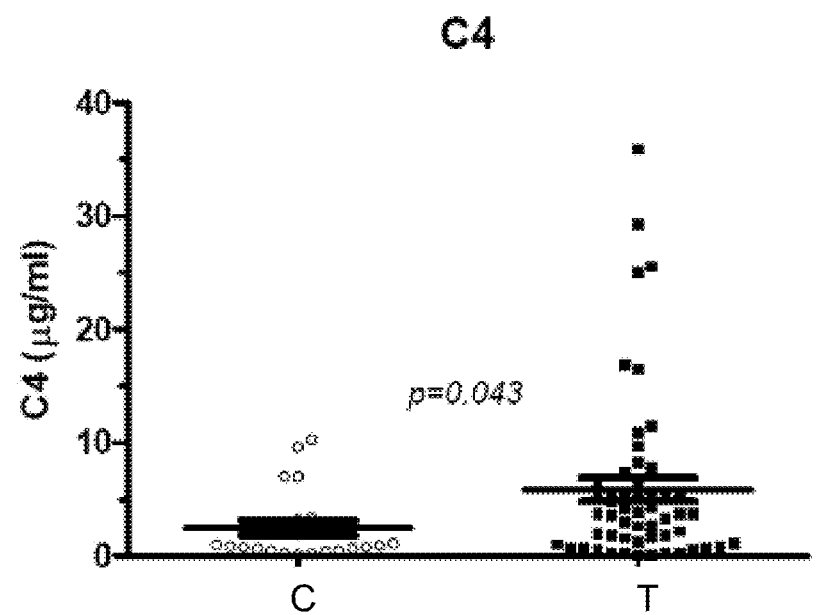
Figure 4:
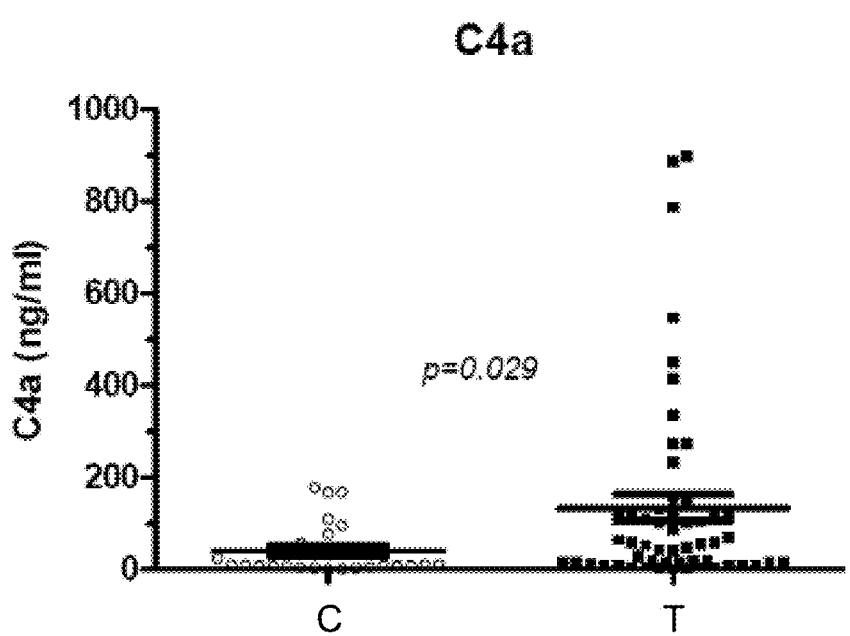
Figure 5:
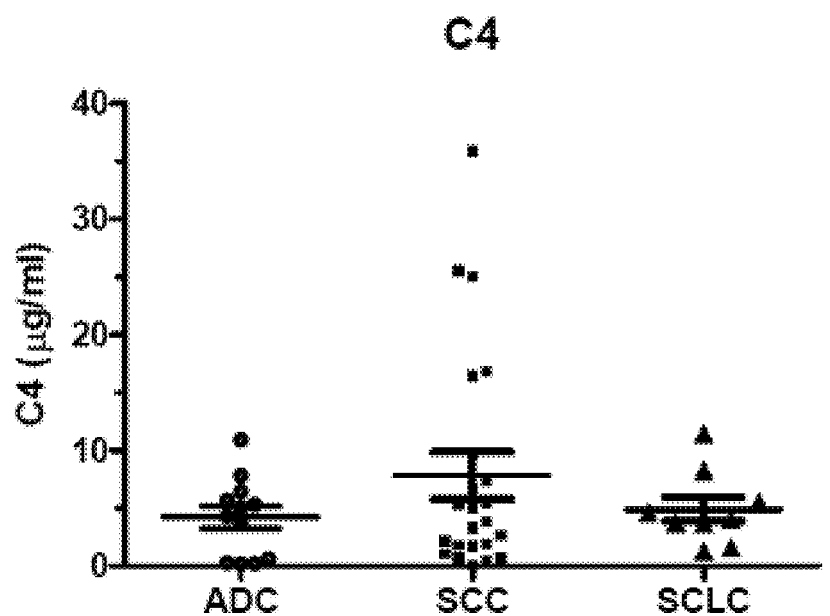
Figure 5:
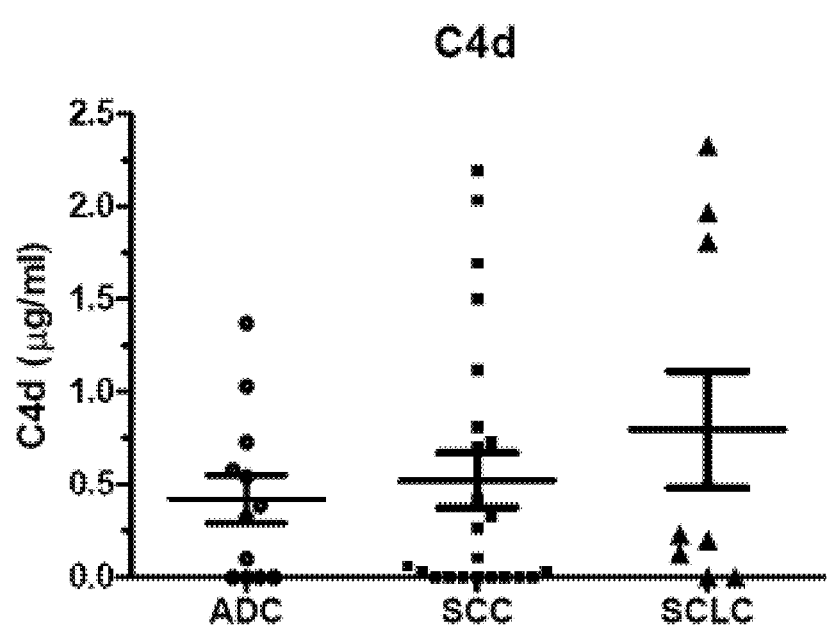

For that purpose, concentrations of C4, C5a, C4d activation fragments and C4a were quantified. C4 and C5a were selected based on their previous implication in cancer. C4d activation fragments and C4a were chosen as specific markers of classical complement activation. Previously, total protein in this series of patients had been determined (Pio R. et al., 2010). Bronchoalveolar lavage supernatants from patients with lung cancer presented significantly higher levels of C4, C4d activation fragments, and C4a than those from non-cancer patients (FIG. 4). Concentrations of all markers in control versus tumor subjects, respectively, were (mean±SD): C4: 2.43±3.12 vs. 5.90±7.59 µg/ml (p=0.013); C5a: 26.33±25.84 vs. 41.37±39.66 ng/ml (p=0.109); C4d activation fragments: 0.16±0.11 vs. 0.59±0.83 µg/ml (p<0.001); C4a: 32.67±44.07 vs. 134.9±212.2 ng/ml (p=0.003). In the cancer group, no differences were found between marker levels and tumor histology (FIG. 5).

It has been previously described that in bronchoalveolar lavage fluids there is a significant increased in plasma proteins such as factor H (Pio R. et al., 2010). Considering this fact, the concentration of the complement components was normalized (divided) by the concentration of factor H. In this analysis, only the levels of C4d activation fragments/factor H and C4a/factor H were different between controls and cancer patients. Data were: C4/factor H: 2.028±1.071 vs. 2.575±2.515 (p=0.596); C5a/factor H: 0.055±0.067 vs. 0.084±0.206 (p=0.787); C4d activation fragments/factor H: 0.091±0.021 vs. 0.218±0.294 (p<0.001); C4a/factor H: 0.027±0.019 vs. 0.045±0.033 (p=0.017). This result demonstrates that the determination of activated elements of the classical complement pathway is substantially different from that of inactive complement components (e.g. C4) or activated elements common to different pathways of activation (e.g. C5a). In the case of C4 and C5a, their increase is likely due to a non-specific increase of plasma proteins in the airway fluids; whereas in the case of C4d activation fragments and C4a, the increase is due to a cancer-related event.

A receiver operating characteristic (ROC) curve was generated for each of the four biomarkers. To avoid the influence of plasma proteins, the concentration of each marker was divided by the concentration of factor H. Results are shown in FIG. 6. C4 and C5a had no capacity to distinguish patients from controls. In contrast, C4d activation fragments allowed for the discrimination between patients and controls. High sensitivities and specificities were obtained at different cut-off values (for example, with a cut-off of 0.00013, sensitivity was 49% and specificity 91%; and with a cut-off of 0.0007, sensitivity was 70% and specificity 81%). C4a, was also useful to differentiate between patients and controls This study proves that airway fluids from lung cancer patients contain higher concentrations of some complement components than airway fluids from patients with benign lung diseases. The study also illustrates the crucial difference in the utility of the determination of complement components previously evaluated (such as C4 or C5a) or specific activated elements of the classical pathway (C4d activation fragments or C4a), which had never been evaluated in biological fluids of cancer patients. Based on these results, it can be concluded that the determination of C4 activation fragments can be used for the diagnosis of lung cancer in airway fluids.

Example 3. C4d Activation Fragments are Increased in Plasma from Lung Cancer Patients at Advanced Stages Material and Methods Plasma samples from fifty patients with advanced lung cancer (stages IIIB and IV) and fifty healthy people, matched by age, sex and smoking history (pack years), were obtained at the Clinica Universidad de Navarra. Lung tumors were classified according to the World Health Organization 2004 classification (Trawis W. D. et al., 2004). The study protocol was approved by the Institutional Ethical Committee, and all patients gave written informed consent.

Determinations of C4, C4d activation fragments and C5a were performed as explained in Example 2. Total protein was measured using the BCA protein assay (23225, Pierce), with bovine serum albumin as the standard. Plasma dilutions were: 1:$10^5$ for C4, 1:50 for C4d activation fragments, 1:100 for C5a, and 1:100 for total protein. Samples below the quantification limit of the kit were assigned a concentration of one-half of the quantification limit.

Results

Activation of the classical complement pathway was evaluated in plasma samples from lung cancer patients at advanced stages (IIIB and IV) and from healthy controls. Both groups were matched by sex, age and smoking history. The concentrations of C4, C4d activation fragments and total protein were quantified. Plasma samples from patients with lung cancer presented significantly higher levels of C4, C4d activation fragments and total protein than those from healthy volunteers (FIG. 7). Concentrations of all markers in control and tumor subjects, respectively, were (mean±SD): C4: 0.73±0.27 vs. 0.96±0.23 mg/ml (p<0.001); C4d activation fragments: 1.86±0.95 vs. 4.13±2.02 µg/ml (p<0.001); total protein: 69.53±9.58 vs. 76.80±11.24 mg/ml (p=0.001). The levels of these molecular markers were not related to age, gender or pack years.

ROC curves were generated for C4 and C4d activation fragments using the software SPSS 15.0 (FIG. 8). The most remarkable differences between cancer patients and normal volunteers were found in the determination of C4d activation fragment levels. In fact, the determination of C4d activation fragment levels was substantially superior that the determination of C4 levels for the discrimination between patients and controls. Remarkably high sensitivities and specificities were obtained at different C4d cut-off values (for example, with a cut-off of 4.00 µg/ml, sensitivity was 46% and specificity 98%; and with a cut-off of 2.00 µg/ml, sensitivity was 90% and specificity 68%).

This study again highlights the substantial difference between the determination of C4 and the determination of C4d activation fragments. Based on these results, it can be concluded that the determination of C4d activation fragments can be used for the diagnosis of lung cancer in blood.

Example 4. C4d Activation Fragments are Increased in Plasma from Patients with Lung Cancer at Early Stages Material and Methods Plasma samples from eighty four patients with surgically resectable lung cancer at early stages (I and II) and from forty five healthy people (matched by age and smoking history) were obtained at the Clinica Universidad de Navarra. Only patients with adenocarcinoma (n=45) or squamous cell carcinoma (n=39) were included. Lung tumors were classified according to the World Health Organization 2004 classification (Trawis W. D. et al., 2004). The study protocol was approved by the Institutional Ethical Committee, and all patients gave written informed consent.

Determinations of C4, C4d, activation fragments and total protein were performed as explained in Example 2 and Example 3.

Results

Activation of the classical complement pathway was evaluated on plasma samples from lung cancer patients at early stages (I and II) and from healthy controls. Both groups were matched by age and smoking history. The concentrations of C4, C4d activation fragments, and total protein were quantified. Plasma samples from patients with lung cancer presented significantly higher levels of C4d activation fragments than those from healthy volunteers (FIG. 9). No differences were found in the levels of C4 and total protein between groups. Concentrations of all markers in control and tumor subjects, respectively, were (mean±SD): C4: 0.94±0.36 vs. 0.89±0.37 mg/ml (p=0.312); C4d activation fragments: 1.13±0.69 vs. 3.18±3.21 µg/ml (p<0.001); total protein: 78.12±11.16 vs. 79.96±24.00 mg/ml (p=0.529). There was no statistical association between the levels of these molecular markers and age, sex, pack years or histology.

ROC curves were generated with data from C4 and C4d activation fragment determinations (FIG. 10). The determination of C4d activation fragments allowed for the discrimination between patients and controls. In contrast, C4 have no capacity to distinguish patients from controls. High sensitivities and specificities were obtained using C4d determination (for example, with a cut-off of 2.40 µg/ml, sensitivity was 44% and specificity 98%).

This analysis evidences that blood from patients with lung cancer at early stages contains higher concentrations of C4d activation fragments but not of C4. Based on these results, it can be concluded that the determination of C4d activation fragments can be used for the diagnosis of lung cancer, even in the case of patients at very early stages of the disease.

Example 5. C4d Activation Fragments are Associated with Lung Cancer Prognosis

Material and Methods

For each patient, levels of C4d activation fragments (obtained in Example 4) were analyzed together with information about the extension and clinical outcome of the disease.

Results

Changes in the expression of a protein do not imply any association with the prognosis of the disease. To evaluate the capacity of C4d activation fragments to predict the outcome of lung cancer patients, the association between the levels of this marker and clinico-pathological characteristics, such as stage, tumor size or survival, was investigated.

First, differences in C4d activation fragment levels in plasma from lung cancer patients in stage I or stage II were evaluated (FIG. 11). Stage I patients (n=65) had significantly lower levels of C4d activation fragments than stage II patients (n=19): 2.80±2.85 vs. 4.49±4.01 µg/ml (p=0.023). Moreover, within stage I, patients in stage IA (n=37) tended to have lower levels of C4d activation fragments than those in stage IB (n=28): 1.96±1.10 vs. 3.89±3.94 µg/ml (p=0.078). No statistical differences were observed (p=0.600) between patients in stage IIA (n=8) and IIB (n=11). No differences were either found when the levels of C4 were compared with stages of the disease: Stage I vs stage II: 0.90±0.38 vs. 0.85±0.34 mg/ml (p=0.554); stage IA vs stage IB: 0.87±0.32 vs. 0.96±0.44 mg/ml (p=0.435).

Differences in T stage (T1 vs. T2/T3), size and in lymph node involvement (NO vs. N1) were also examined. C4d activation fragment levels were higher in patients with T2/T3 stages (4.05±4.02 µg/ml; n=39) than in patients with T1 stage (2.42±2.04 µg/ml; n=45), although the differences did not reach statistical significance (p=0.118). In addition, there was a significant correlation between tumor size and C4d activation fragment levels (Spearman's rank correlation=0.37; p=0.001). In the case of the N status, levels in patients with NO tumors (2.77±2.81 µg/ml; n=68) were significantly lower than in patients with N1 tumors (4.84±4.22 µg/ml: n=16) (p=0.017). In the case of C4, no differences between T stages (0.87±0.32 vs. 0.95±0.43 mg/ml, p=0.791) or N status (0.89±0.38 vs. 0.89±0.35 mg/ml, p=0.991) were found.

Finally, the clinical outcome of the patients was compared with the levels of C4d activation fragments or C4 in plasma (FIG. 12). High levels of C4d activation fragments were significantly associated with worse lung cancer-specific survival (p<0.001). No association was found between survival and the levels of C4.

Therefore, it can be concluded that the determination of C4d activation fragments can be used for the prognosis of patients with lung cancer.

Example 6. C4d Activation Fragments can be Used to Identify Individuals with a High Risk to Develop Lung Cancer Material and Methods Levels of C4d activation fragments were determined in plasma from a nested cohort of asymptomatic individuals with or without lung cancer.

Plasma samples from individuals enrolled at the Clinica Universidad de Navarra in a CT screening study were used. Eligibility criteria for the screening program included age ≥40 years, and >10 pack-year smoking history. Subjects with symptoms of lung cancer were excluded from the screening program. The study protocol has been previously published (Henschke C I et al., 1999) and was approved by the Institutional Ethical Committee. All patients gave written informed consent. The complete series included more than 2500 high risk individuals.

Thirty two people diagnosed with lung cancer after the completion of the screening protocol were selected based on sample availability. Each of these cases was matched by age, gender and smoking history with four to five cancer-free subjects obtained from the same cohort of people (158 controls in total).

Determination of C4d activation fragments in plasma samples diluted 1:50 was performed as explained in Example 2.

The Cochran-Mantel-Haenszel test was used to estimate odds ratios (OR) and 95% confidence intervals for the association of lung cancer risk with C4d activation fragment levels categorized in high and low using different cut-offs (1, 1.5 and 2 µg/ml) and adjusted for age, sex and smoking history (pack-years).

Results

C4d activation fragment levels were determined in plasma samples from 115 asymptomatic high risk individuals. Thirty two of them were diagnosed with lung cancer in the context of a CT screening program. The concentration of C4d activation fragments was quantified in all cases. Marker levels in individuals with lung cancer were significantly higher than in those without lung cancer: 1.80±1.36 µg/ml vs. 0.80±0.47 µg/ml (p<0.001).

Association with lung cancer risk was evaluated using a conditional logistic regression. C4d activation fragment levels were dichotomized using 1, 1.5 and 2 µg/ml as the cut-off. Individuals with high marker levels showed a statistically significant increased risk of lung cancer compared with those with low levels: cut-off 1 µg/ml: OR=5.79 (95% CI=2.43-13.76, p<0.001); cut-off 1.5 µg/ml: OR=9.26 (95% CI=3.26-26.27, p<0.001); cut-off 2 µg/ml: OR=54.18 (95% CI=7.01-418.84, p<0.001).

This analysis evidences that the determination of C4d activation fragments is a useful biomarker for assessment of lung cancer risk in asymptomatic individuals.

Example 7. C4d Activation Fragments can be Used as a Biomarker for Treatment Efficacy, to Monitor Response to Treatment and Progress of the Disease Material and Methods The capacity of C4d activation fragments, as a molecular indicator of classical complement activation, to monitor response to treatment was evaluated in lung cancer patients before and after surgical removal of the tumor.

Nineteen patients with resectable lung cancer were included in the study. From each patient, plasma samples before and after complete surgical removal of the tumor (pre-treatment and post-treatment samples, respectively) were used. Patients were selected on the basis of sample availability and previous determinations of C4d activation fragment levels in the pre-treatment sample (in all selected patients, C4d activation fragment levels in pre-treatment plasma were higher than 2 µg/ml). For the post-treatment samples, the median number of months after surgery was 7 months (range: 4-44 months). Samples were obtained at the Clinica Universidad de Navarra. The study protocol was approved by the Institutional Ethical Committee, and all patients gave written informed consent.

Determination of C4d activation fragments in plasma samples diluted 1:50 was performed as explained in Example 2.

Results

In most cases, C4d activation fragment levels were dramatically reduced after surgical removal of the tumor (FIG. 13). In fact, in more than 70% of the cases (14 out of 19) the levels of C4d activation fragments dropped below the quantification limit of the assay. This observation was independent of the elapsed time between surgery and the collection of the follow-up sample.

This result evidences that C4d activation fragments can be used as a cancer biomarker to assess treatment efficacy and monitor progress of the disease.

In summary, all these experimental results evidence that C4 activation fragments, and particularly C4d activation fragments, can be used as a diagnostic-prognostic tool for lung cancer, with outstanding sensitivity and specificity over other complement component molecules.

REFERENCES CITED IN THE APPLICATION

Aberle D. R. et al., "Reduced lung-cancer mortality with low-dose computed tomographic screening", N. Engl. J. Med., 2011, vol. 365, pp. 395-409.

Burtis C. A. et al., "Tietz Fundamentals of Clinical Chemistry", Chapter 14: Establishment and Use of Reference values, Saunders/Elsevier, 6$^{th}$ edition, St Louis, 2008, pp. 229-238)

Henschke C. I. et al., "Early Lung Cancer Action Project: overall design and findings from baseline screening", Lancet, 1999, vol. 354, p. 99-105.

Henschke C. I. et al., "Survival of patients with stage I lung cancer detected on CT screening", N. Engl. J. Med., 2006, vol. 355, pp. 1763-1771.

Hou et al., "Preparation of C4 antiserum and detection of complement C4 activation in plasma with crossed immunoeletrophoresisi", 1985, Zhongguo Yixue Kexueyuan Xuebao, vol. 7, pp 473-474.

Niehans G. A. et al., "Human carcinomas variably express the complement inhibitory proteins CD46 (membrane cofactor protein), CD55 (decay-accelerating factor), and CD59 (protectin)", Am. J. Pathol., 1996, vol. 149, pp. 129-142.

Nishioka K. et al., "The complement system in tumor immunity: significance of elevated levels of complement in tumor bearing hosts", Ann. N. Y. Acad. Sci., 1976, vol. 276, pp. 303-315.

Oner F. et al., "Immunoglobulins and complement components in patients with lung cancer", *Tuberk Toraks,* 2004, vol. 52, pp. 19-23.

Pio R. et al., "Complement factor H is elevated in bronchoalveolar lavage fluid and sputum from patients with lung cancer", *Cancer Epidemiol. Biomarkers Prev.,* 2010, vol. 19, p. 2665-2672.

Travis W. D. et al., World Health Organization Classification of Tumours. Pathology and Genetics of Tumours of the Lung, Pleura, Thymus and Heart. Lyon: IARC Press; 2004.

The invention claimed is:

1. A method of diagnosis and/or prognosis of lung cancer in a subject, the method comprising:
   a) imaging the subject for lung cancer, wherein the imaging is CT-scanning;
   b) determining, in vitro, the level of a C4 activation fragment in a test sample from the subject by contacting the test sample with a reagent that selectively binds the C4 activation fragment;
   c) comparing the level determined in step b) with a reference control level of said C4 activation fragment; wherein the steps a) and b) can be performed in any order; and wherein the C4 activation fragment is C4a or C4d and does not comprise C4; and
   d) providing a diagnosis that the subject suffers from lung cancer and/or has a had prognosis of lung cancer if the level of the C4 activation fragment as determined in step (b) is higher than the reference control level.

2. The method according to claim 1, wherein the lung cancer is selected from the group consisting of non-small cell lung cancer and small-cell lung carcinoma.

3. The method according to claim 1, wherein the C4 activation fragment is a C4d activation fragment comprising SEQ ID NO:1 or 2.

4. The method according to claim 1, wherein the level of C4a is determined.

5. The method according to claim 1, wherein contacting the test sample with a reagent that binds the C4 activation fragment comprises performing an immunoassay.

6. The method of claim 1 further comprising recommending treatment for lung cancer.

7. The method of claim 1 wherein the C4 activation fragment is produced by proteolysis of C4.

8. The method of claim 1 wherein the C4 activation fragment consists of the amino acid sequence of a C4 activation fragment protein.

9. The method of claim 1 wherein the reagent is one or more antibodies able to selectively bind the C4 activation fragment.

10. A method for identifying a subject suspected of suffering from lung cancer, the method comprising:
    a) imaging the subject for lung cancer, wherein the imaging is CT-scanning;
    b) determining, in vitro, the level of a C4 activation fragment in a test sample from the subject by contacting the test sample with a reagent that selectively binds the C4 activation fragment;
    c) comparing the level of step b) with a reference control level, wherein the steps a) and b) can be performed in any order; and wherein the C4 activation fragment is C4a or C4d and does not comprise C4; and
    d) identifying that the subject is suspected of suffering from lung cancer if the level of the C4 of fragment as determined in step (b) is higher than the reference control level, identifying that the subject is suspected of suffering from lung cancer.

11. The method according to claim 10, wherein the lung cancer is selected from the group consisting of non-small cell lung cancer and small-cell lung carcinoma.

12. The method according to claim 10, wherein the C4 activation fragment is a C4d activation fragment comprising SEQ ID NO:1 or 2.

13. The method according to claim 10, wherein the level of C4a is determined.

14. The method according to claim 10, wherein contacting the test sample with a reagent that binds the C4 activation fragment comprises performing an immunoassay.

* * * * *